US009386979B2

(12) United States Patent
Ferreira

(10) Patent No.: US 9,386,979 B2
(45) Date of Patent: Jul. 12, 2016

(54) ENDOSCOPIC SUTURING DEVICE WITH SUTURE MANAGEMENT

(75) Inventor: Danial P. Ferreira, Milford, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 1402 days.

(21) Appl. No.: 13/126,616

(22) PCT Filed: Oct. 28, 2008

(86) PCT No.: PCT/US2008/012233
§ 371 (c)(1),
(2), (4) Date: Oct. 18, 2011

(87) PCT Pub. No.: WO2010/050910
PCT Pub. Date: May 6, 2010

(65) Prior Publication Data
US 2012/0022560 A1  Jan. 26, 2012

(51) Int. Cl.
A61B 17/04 (2006.01)
A61B 1/00 (2006.01)
A61B 17/30 (2006.01)
A61B 17/06 (2006.01)

(52) U.S. Cl.
CPC ......... A61B 17/0469 (2013.01); A61B 1/00087 (2013.01); A61B 1/00101 (2013.01); A61B 17/0482 (2013.01); A61B 17/0491 (2013.01); A61B 17/06123 (2013.01); A61B 2017/0496 (2013.01); A61B 2017/306 (2013.01)

(58) Field of Classification Search
CPC ..................... A61B 2017/306; A61B 17/0482; A61B 17/0469; A61B 17/04; A61B 17/0491; A61B 17/06123
See application file for complete search history.

(56) References Cited

U.S. PATENT DOCUMENTS 373,372 A    11/1887  King
3,638,653 A *  2/1972  Berry ............................ 606/146
3,842,840 A   10/1974  Schweizer
(Continued)

FOREIGN PATENT DOCUMENTS

EP        1 852 071 A2    11/2007
WO       WO 97/10756 A1    3/1997
WO     WO 2004/103189 A1  12/2004

OTHER PUBLICATIONS

Office Action for Canadian Patent Application No. 2,741,713, mailed Nov. 28, 2014 (4 pages).
(Continued)

Primary Examiner — Gregory Anderson
Assistant Examiner — Christina Lauer
(74) Attorney, Agent, or Firm — Wolf, Greenfield & Sacks, P.C.

(57) ABSTRACT

An endoscopic tissue suturing device may include a suturing head configured to capture tissue at a tissue capture region. A needle can move through the region to place stitches in the tissue. A control handle includes an actuator coupled to the needle. The control handle supports a suture spool about an axis of rotation. The axis of the spool may be parallel to the direction of movement of the actuator. The spool surface may be tapered at an angle relative to the axis of rotation. A spool end wall may be configured to urge the spool in an axial direction. The handle may provide external access to a portion of the suture. A cover may be provided to cover the spool. The cover may be rotatably supported on the handle independent of the spool. Suture material may be wound onto the spool by rotating the cover.

69 Claims, 17 Drawing Sheets

(56) References Cited

U.S. PATENT DOCUMENTS

| | | | |
|---|---|---|---|
| 4,164,225 | A | 8/1979 | Johnson et al. |
| 4,841,888 | A | 6/1989 | Mills |
| 5,037,021 | A | 8/1991 | Mills |
| 5,080,663 | A | 1/1992 | Mills |
| 5,350,385 | A | 9/1994 | Christy |
| 5,792,153 | A | 8/1998 | Swain |
| 5,797,927 | A | 8/1998 | Yoon |
| 6,443,963 | B1 | 9/2002 | Baldwin et al. |
| 6,786,913 | B1 | 9/2004 | Sancoff et al. |
| 6,951,565 | B2 | 10/2005 | Keane et al. |
| 7,048,748 | B1 | 5/2006 | Ustuner |
| 7,131,979 | B2 | 11/2006 | DiCarlo et al. |
| 7,169,157 | B2 | 1/2007 | Kayan |
| 7,232,446 | B1 | 6/2007 | Farris |
| 7,862,582 | B2 | 1/2011 | Ortiz et al. |
| 2003/0171760 | A1 | 9/2003 | Gambale |
| 2003/0204195 | A1* | 10/2003 | Keane et al. .................. 606/146 |
| 2003/0208209 | A1 | 11/2003 | Gambale |
| 2005/0033319 | A1* | 2/2005 | Gambale et al. .............. 606/139 |
| 2006/0155307 | A1 | 7/2006 | Rosch |
| 2007/0093854 | A1 | 4/2007 | Kayan |
| 2008/0097483 | A1 | 4/2008 | Ortiz et al. |
| 2011/0077671 | A1 | 3/2011 | Ortiz et al. |

OTHER PUBLICATIONS

International Search Report and Written Opinion of the International Searching Authority for International Application No. PCT/US2008/012233, dated Dec. 30, 2008. (13 pages).

Extended European Search Report dated Jul. 17, 2015 for EP 08 87 7835 (10 pages).

* cited by examiner

ENDOSCOPIC SUTURING DEVICE WITH SUTURE MANAGEMENT

CROSS-REFERENCE TO RELATED APPLICATIONS

This application is a national stage filing under 35 U.S.C. §371 of International Application No. PCT/US2008/012233, filed Oct. 28, 2008, which is incorporated by reference in its entirety.

BACKGROUND OF INVENTION

1. Field of Invention

The present invention relates to a device and methods for securing tissue of the human body, and more particularly relates to an endoscopic suturing device for endoscopically suturing tissue with minimally invasive techniques.

2. Discussion of Related Art

Endoscopic apposition devices can be used in the body of a patient without the need to make an external incision in the patient. The device is controlled outside the patient by endoscopic techniques. The device may comprise a sewing or stapling device for use in flexible endoscopy, although it is also applicable to devices for use in rigid endoscopy.

Endoscopic apposition devices have been found to be useful in the treatments of the digestive system, with the endoscope being transorally inserted through a patient's esophagus. For example, such devices have been found useful in treating gastroesophageal reflux disease (GERD) by placing stitches to form tissue plications at the junction of the esophagus and stomach. The minor anatomical change resulting from the plication formation appears to relieve the symptoms of GERD in some patients. It is also being proposed to employ such devices in treating obesity by placing stitches to segregate portions of a stomach or revise prior surgical procedures.

Endoscopic sewing devices of this general type are described in, for example, U.S. Pat. Nos. 5,080,663 and 5,792,153, which disclose a sewing device for passing a thread or suture through a tissue portion. The sewing device comprises a hollow needle movable between a first position in which it is out of the tissue portion and a second position in which it passes through the tissue portion, and a thread carrier adapted to be attached to the thread and being receivable within the hollow needle. The sewing device also comprises a body which defines a cavity within which the tissue portion can be held by suction. The hollow needle is mounted for movement in the body between the first and second positions.

The sewing devices include a single stitch sewing device and a multiple stitch sewing device. In the single stitch device, the thread carrier is transported by the needle through the tissue as the needle passes from its first position to its second position. When the needle returns to its first position, the thread carrier is maintained in the distal end of the sewing capsule. In the multiple stitch device, the same procedure occurs, but it is followed by a further step in which the hollow needle travels from its first position to its second position, picks up the thread carrier, and returns it to the first position. A second stitch may be formed during the next step. The whole sequence of steps is repeated as many times as may be required to form the desired number of stitches.

After placement of the sutures through the tissue, the suture can be secured tightly by knots or by a mechanical locking device. U.S. application Ser. No. 10/220,413 ("Suture Clips, Delivery Devices and Methods", filed Mar. 13, 2003) and Ser. No. 10/275,534 ("Tissue Capturing and Suturing Device and Method", filed Nov. 6, 2002), which are incorporated by reference herein in their entirety, disclose mechanical locking devices for securing a suture in an internal body location that are deliverable by an endoscope.

When using sewing devices, such as those identified above, the suture is typically handled separately from the sewing device during a suturing procedure. It would be desirable to provide an endoscopic tissue apposition device that includes a suture management arrangement that provides and manages a supply of suture for placing one or more stitches during a single intubation.

SUMMARY OF INVENTION

In one illustrative embodiment, an endoscopic tissue suturing device comprises a suturing capsule that is mountable to a distal end of an endoscope and includes a tissue suction chamber that is adapted to capture tissue therein when a vacuum is applied thereto. The suturing device also comprises a needle that is movable within the suturing capsule along a pathway that extends through the tissue suction chamber. The needle is adapted to penetrate tissue captured within the tissue suction chamber when the needle is extended in a distal direction from a proximal end to a distal end of the suturing capsule. The suturing device further comprises a control handle that is mountable to a proximal end of the endoscope and is coupled to the needle and constructed and arranged to control movement of the needle within the suturing capsule. The suturing device also comprises a suture supply that is supported by the control handle and includes a length of suture that is coupled to the needle to form one or more stitches in tissue.

In another illustrative embodiment, an endoscopic tissue suturing device comprises a suturing head that is endoscopically insertable into a patient and is constructed and arranged to capture tissue at a tissue capture region thereof. The suturing device also comprises a needle that is movable along a pathway that extends through the tissue capture region and is adapted to penetrate tissue captured at the tissue capture region when the needle is extended in a distal direction from a proximal end to a distal end of the suturing head. The suturing device further comprises a control handle including an actuator that is coupled to the needle and movable in a first direction to control movement of the needle relative to the tissue capture region, and a suture spool rotatably supported by the control handle about an axis of rotation that is parallel to the first direction. The suture spool includes a length of suture that is coupled to the needle to form one or more stitches in tissue.

In a further illustrative embodiment, an endoscopic tissue suturing device comprises a suturing head that is endoscopically insertable into a patient and is constructed and arranged to capture tissue at a tissue region thereof. The suturing device also comprises a needle that is movable along a pathway that extends through the tissue capture region and is adapted to penetrate tissue captured at the tissue capture region when the needle is moved along the pathway. The suturing device further comprises a control handle including an actuator that is coupled to the needle to control movement of the needle relative to the tissue capture region, and a suture spool including a length of suture that is coupled to the needle to form one or more stitches in tissue. The suture spool is rotatably supported by the control handle about an axis of rotation. The suture spool includes a bottom wall with a surface about which the suture is wound, and the surface of the bottom wall is tapered at an angle relative to the axis of rotation.

In another illustrative embodiment, an endoscopic tissue suturing device comprises a suturing head that is endoscopically insertable into a patient and is constructed and arranged to capture tissue. The suturing device also comprises a needle that is movable along a pathway that extends through a tissue capture region of the suturing head and is adapted to penetrate tissue captured at the tissue capture region when the needle is moved along the pathway. The suturing device further comprises a control handle including an actuator that is coupled to the needle to control movement of the needle relative to the tissue capture region, and a suture spool including a length of suture that is coupled to the needle to form one or more stitches in tissue. The suture spool is rotatable about an axis of rotation. The suture spool includes a bottom wall with a surface about which the suture is wound and an end wall located at an end of the bottom wall to retain the suture on the suture spool. The end wall is constructed and arranged to urge the suture spool in an axial direction along the axis of rotation.

In a further illustrative embodiment, an endoscopic tissue suturing device comprises a suturing head that is endoscopically insertable into a patient and is constructed and arranged to capture tissue. The suturing device also comprises a needle that is movable along a pathway that extends through a tissue capture region of the suturing head and is adapted to penetrate tissue captured at the tissue capture region when the needle is moved along the pathway. The suturing device further comprises a control handle including an actuator that is coupled to the needle to control movement of the needle relative to the tissue capture region, and a suture spool including a length of suture that is coupled to the needle to form one or more stitches in tissue. The suture spool is rotatably housed within the control handle about an axis of rotation. The control handle is configured to provide external access to a portion of the suture.

BRIEF DESCRIPTION OF DRAWINGS

Various embodiments of the invention will now be described, by way of example, with reference to the accompanying drawings, in which.

DETAILED DESCRIPTION

Figure 1:
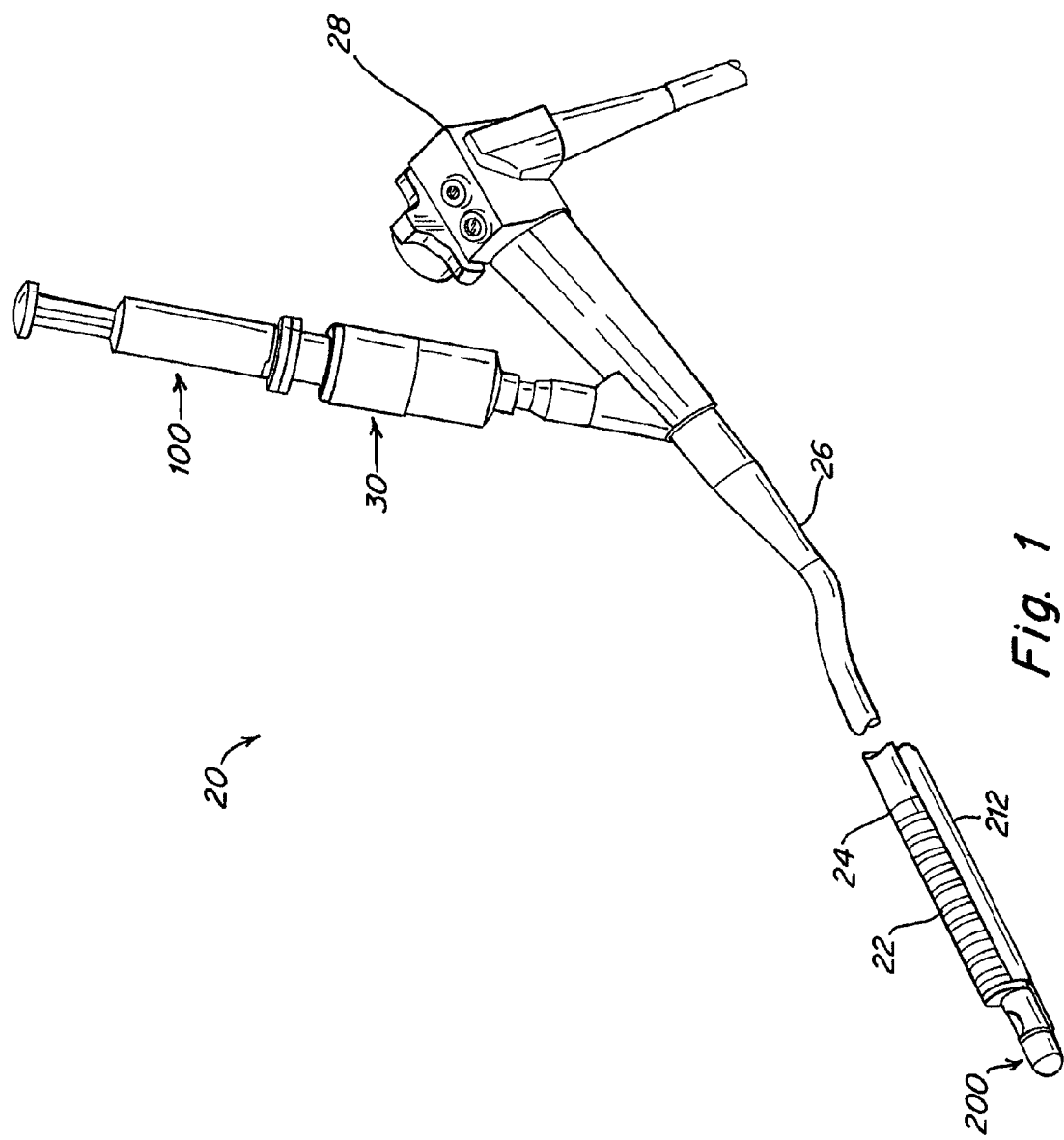
FIG. 1 is a perspective view of an endoscopic suturing device according to one illustrative embodiment employed with an endoscope.

The present invention is directed to an endoscopic suturing device that can be employed to suture tissue using endoscopic techniques. The suturing device may be used for endoscopically placing one or more stitches in tissue or muscle within a cavity or organ of a patient. For example, the suturing device may be particularly suited for treating various gastrointestinal or bariatric conditions, such as GERD and obesity. The suturing device may be used in conjunction with any of various conventional endoscopes, although aspects of the device may be integrated with an endoscope configured specifically for endoscopic suturing procedures.

To facilitate the placement of multiple stitches during a single intubation, the suturing device may include a supply of suture that is sufficient to form any number of stitches that may be desired during a suturing procedure without requiring reloading the suturing device. The suturing device may be configured to store the suture so that it can be fed to the needle in a smooth, controlled manner during a suturing procedure.

The suturing device may include a suturing head that is configured to capture tissue that is to be sutured with the device. The suturing head may include a tissue capture region for capturing one or more portions of tissue. In one embodiment, the suturing head may include a capsule with a suction chamber into which is drawn tissue via a vacuum. However, the device may employ other arrangements for capturing tissue as would be apparent to one of skill in the art.

The suturing device may include a needle to penetrate and place suture through captured tissue. The needle may be movable along a pathway that extends through the tissue capture region of the suturing head. In one embodiment, the needle may be arranged so that it can be moved in a longitudinal direction across the suction chamber to penetrate and place stitches in the captured tissue. The needle may be positioned in the suturing head through a working channel of the endoscope. However, the device may employ other needle arrangements for penetrating tissue captured by the device as would be apparent to one of skill in the art.

The suturing device may include a control handle that is coupled to the needle to control movement of the needle during a suturing procedure. The control handle may include an actuator that can be actuated by a user to operate the suturing device.

The suturing device may include a supply of suture that is coupled to the needle for making one or more stitches in tissue. In one embodiment, the suture supply is provided on the control handle, although the suturing device is not limited in this manner.

The suturing device may include a suture spool that is wound with a length of suture that is coupled to the needle. The spool preferably holds a length of suture that is capable of forming any number of stitches as may be required during a single intubation of the endoscope without reloading the device. Such an arrangement may be desirable to store the suture in a compact and organized fashion that feeds suture to the needle in a smooth, controlled manner during a suturing procedure.

The suture spool may be rotatably supported by the control handle about an axis of rotation. In one embodiment, the suture spool is supported so that it can rotate freely in both rotational directions. In this regard, the suturing device may be configured without a locking arrangement that could prevent rotation in one or both rotational directions. However, if desired, a locking or ratcheting arrangement may be employed to limit or restrict rotation of the suture spool.

The control handle may include an actuator that is configured to be moved in a first direction to control movement of the needle relative to the tissue capture region. In one embodiment, the suture spool rotates about an axis of rotation that is parallel to the first direction. The actuator may be configured to slide in a linear direction. The suture spool may be positioned coaxial with the actuator, and the suture spool may be located about the actuator. It is to be appreciated that other actuator arrangements may be implemented with the suturing device.

In one embodiment, the spool is located within an annular channel provided on the control handle. The suture may be routed from the spool and through the control handle along one or more internal passageways to a distal end of the handle where it can then be extended to the needle. In this manner, the suture may be maintained internal to the suturing device to provide a suture management arrangement that may help reduce the potential for the suture becoming snagged or entangled during a suturing procedure.

The suture spool may include a bottom wall with a surface about which the suture is wound and an end wall located at an end of the bottom wall which may help retain the suture on the suture spool. The spool may be configured so that it fits snugly within the channel and rotates smoothly to feed out suture material during a suturing operation.

In one embodiment, the bottom wall surface is tapered at an angle relative to the axis of rotation to facilitate uniform winding of the suture onto the suture spool. The bottom wall surface may be angled so that it rises away from the axis of rotation in a direction from a proximal end of the spool to the distal end of the spool. This arrangement may also facilitate unwinding the suture from the spool as the suture is drawn in the distal direction during a suturing procedure.

In one embodiment, the end wall is configured to urge the suture spool in an axial direction along the axis of rotation. At least a portion of the end wall may be angled so that it exerts a biasing force against one side of the channel to urge the spool in the axial direction and against the opposite side of the channel. This arrangement may help close up potential gaps or spaces between the spool and the channel that could otherwise catch or snag the suture. The end wall may be oriented at an angle that is non-perpendicular to the axis of rotation. If desired, the entire end wall may be oriented at an angle.

The end wall may be configured as a flexible or resilient member that exerts a spring-like force for urging the spool in the axial direction. The end wall may be located at the proximal end of the bottom wall to bias the spool in the distal direction.

The control handle may be configured to allow access to at least a portion of the suture so that a user may, if desired, place tension on the suture during a suturing procedure and/or pay out a length of suture from the spool. In one embodiment, the control handle includes a suture access cavity that provides external access to a portion of the suture that may be grasped and manipulated by a user. The suture may pass through the cavity as it travels from the spool to the needle. It is to be appreciated that external suture access is not required with each embodiment of the suturing device.

A cover may be provided on the control handle to cover and help manage and/or protect the suture. In one embodiment, the cover is configured to overlie the annular spool channel provided in the control handle. The cover may be configured to facilitate winding suture onto the spool. The cover may be rotatably supported on the control handle independent of the spool so that suture material can be coupled to the cover and wound onto the spool by rotating the cover relative to the spool.

The cover may be configured so that it covers the suture access cavity when oriented in a first position and allows access to the cavity when oriented in a second position. In one embodiment, the cover includes an access region that corresponds to the cavity configuration so that the cavity is uncovered and becomes accessible when the cover is rotated to align the access region with the cavity.

The suturing device may include a catch that is located distal to the tissue capture region to receive and retain the suture during a stitching sequence. The catch may be positioned coaxial with the needle to receive the suture when the needle is extended across the tissue capture region.

The suturing device may include a suture tag that is attached to the suture. The suture tag facilitates passage of the suture through tissue and retention of the suture by the catch. In this regard, the suture tag may be carried by the needle through tissue and into the catch. A locking arrangement may be provided to secure the suture tag to the needle and to release the suture tag from the needle during the stitching sequence.

The catch may be configured to receive the suture tag when the needle is extended across the tissue capture region and into the catch, and then retain the suture tag when the suture tag lock is unlocked and the needle is withdrawn from the catch and retracted across the tissue capture region. In this regard, the catch may be configured to strip the suture tag from the needle.

The catch may include a tag locking clip that is configured to receive and retain the suture tag. In one embodiment, the clip may include at least a pair of resilient fingers that are configured to open and close in a radial direction to receive and retain the suture tag. The fingers may be configured so that they are biased in an inward radial direction to a closed position to retain the suture tag and expand outwardly to an open position against the radial biasing force to receive and release the tag.

The catch may be configured to open and release the suture tag when the tag is locked to the needle and retracted in a direction away from the catch.

In one embodiment, the suture tag may be configured to be supported and secured about the exterior surface of the needle. A suture tag lock may be provided between the suture tag and the needle with the lock being actuatable between a locked position to secure the suture tag to the needle and an unlocked position to release the suture tag from the needle. The suture tag lock may include a locking sleeve that is actuatable between the locked and unlocked positions by expanding and reducing a portion of the sleeve by way of relative sliding movement between the needle and sleeve.

In one illustrative embodiment shown in FIG. 1, the endoscopic suturing device 20 includes a control handle 100 and a suturing head 200 that may be releasably secured to the distal end 22 of an endoscope 24. The control handle 100, which may be releasably mounted to the proximal end 26 of the endoscope 24, is coupled to a suturing mechanism that is positioned within the head 200. The suturing mechanism includes a needle (not shown) that may pass through a working channel of the endoscope and into the head.

Operation of the suturing mechanism within a patient may be carried out through actuation of the control handle 100. As shown, the control handle may be mounted adjacent the endoscope control handle 28. The suturing device operates to place sutures through tissue at internal locations within a patient accessible by an endoscope.

As illustrated, the control handle 100 may be coupled to the endoscope with an adjustable tool coupling 30 that facilitates the placement and positioning of the suturing device in the endoscope. One example of a tool coupling that may be particularly suited for use with the suturing device is disclosed in U.S. Pat. Publication 2007/0270640, which is incorporated herein by reference. However, it is to be appreciated that other couplings, if even desired, may be used as would be apparent to one of skill in the art.

Suture Management

To facilitate the formation of multiple stitches during a single intubation, the suturing device may include a supply of suture that is sufficient to form any number of stitches that may be desired during a suturing procedure without requiring reloading the suturing device. The suturing device may be configured to store the suture so that it can be fed to the needle in a smooth, controlled manner during a suturing procedure.

Figure 2:
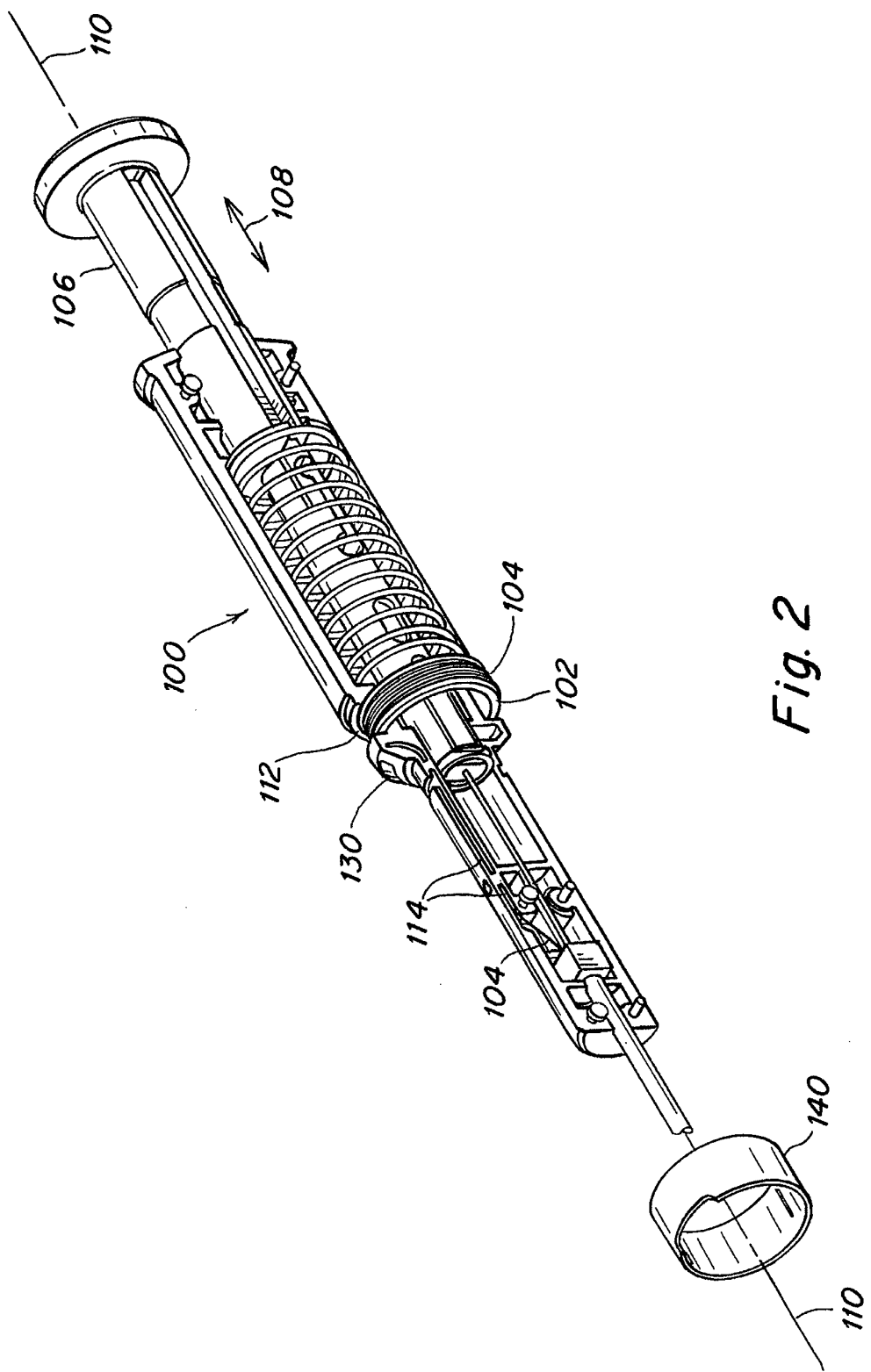
FIG. 2 is a perspective view of the control handle of the suturing device of FIG. 1 according to one illustrative embodiment with a portion of the housing removed to illustrate internal components of the control handle.

In one illustrative embodiment shown in FIG. 2, the suture supply is provided on the control handle 100. The suturing device includes a suture spool 102 that is wound with a length of suture 104 that is coupled to the needle (not shown). The spool holds a length of suture that is capable of forming any number of stitches as may be required during a single intubation of the endoscope without reloading the device. Such an arrangement may be desirable to store suture in an organized fashion that can be easily unwound and fed to the needle.

The suture spool 102 is rotatably supported by the control handle to facilitate winding and unwinding of the suture material onto and from the spool. In one embodiment, the suture spool is freely rotatable in both clockwise and counterclockwise directions. In this regard, it is not required to unlock the spool to allow rotation in either direction. However, it is to be understood that a locking arrangement may be employed to limit or restrict rotation of the suture spool as would be apparent to one of skill in the art.

The control handle 100 may include an actuator that is configured to control movement of the needle relative to the tissue capture region. In one illustrative embodiment shown in FIG. 2, the actuator 106 employs a plunger-like arrangement in which the actuator is configured to slide in a first or linear direction 108 to actuate the needle (not shown) to extend across the suturing capsule. The suture spool 102 is arranged on the handle to rotate about an axis of rotation 110 that is parallel to the actuation direction 108 of the actuator. This arrangement allows the suture 104 to be easily drawn from the spool in a controlled manner. To provide a relatively compact configuration, the suture spool 102 may be positioned coaxial with the actuator 106 with the suture spool located about the actuator. However, it is to be appreciated that other actuator arrangements may be implemented with the suturing device as would be apparent to one of skill in the art.

Figure 3:
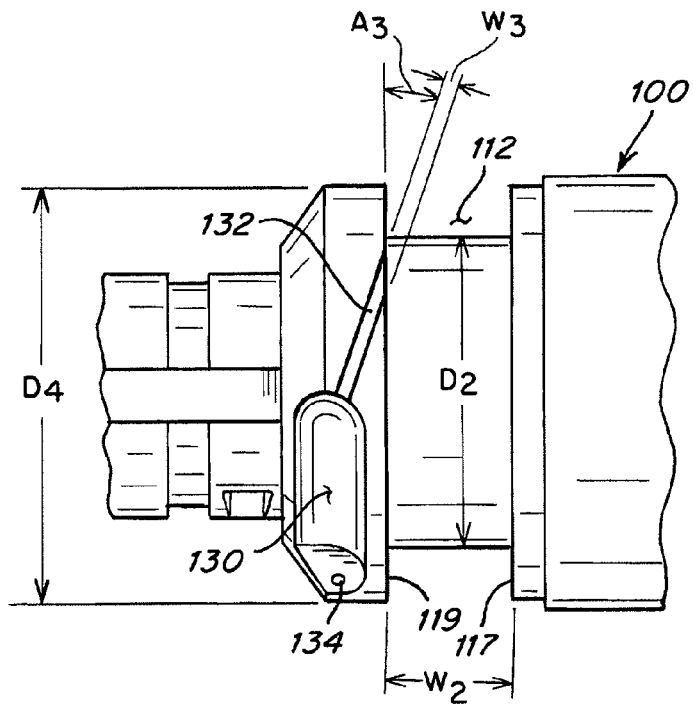
FIG. 3 is an enlarged plan view of a portion of the control handle of FIG. 2 illustrating a suture spool channel and a suture access cavity of a suture management arrangement according to one illustrative embodiment.
Figure 4:
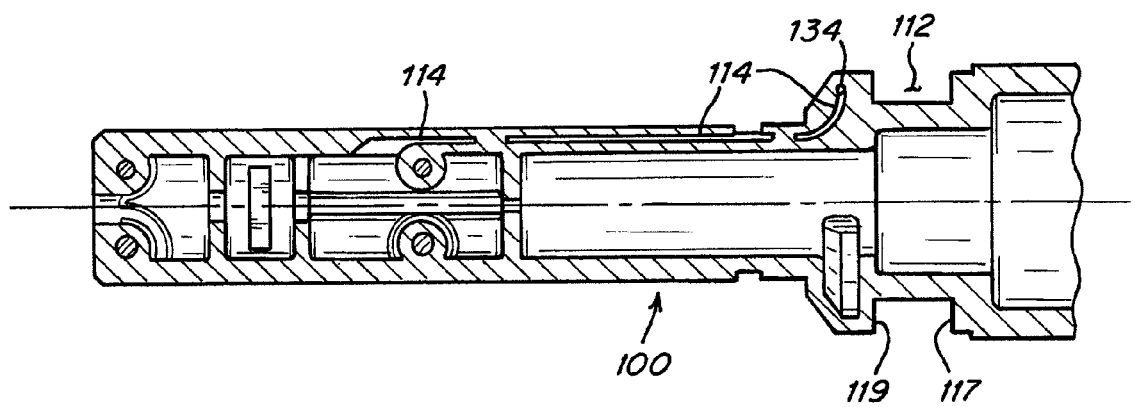
FIG. 4 is a cross-sectional view of the distal portion of the control handle of FIG. 2 illustrating internal suture passageways.
Figure 5:
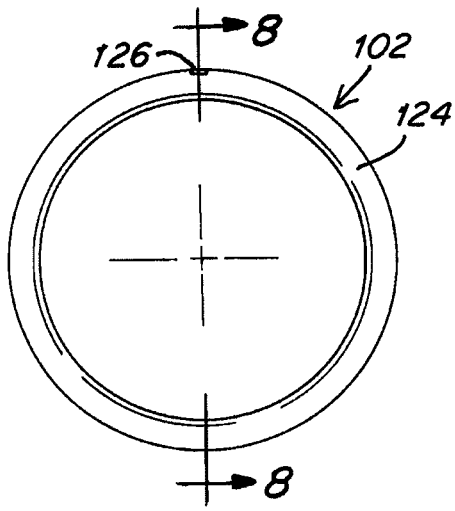
FIG. 5 is an end view of the distal end of a suture spool according to one illustrative embodiment.

In one illustrative embodiment shown in FIGS. 2-4, the spool 102 is located within an annular channel 112 provided on the control handle. The suture 104 may be routed from the spool and through the control handle along one or more passageways 114 to a distal end of the handle where the suture then extends to the needle. In this manner, the suturing device may be configured with a suture management arrangement that may help reduce the potential for the suture becoming snagged or entangled during a suturing procedure.

In one illustrative embodiment shown in FIGS. 5-9, the suture spool 102 includes a bottom wall 116 with a surface 118 about which the suture 104 is wound and an end wall 120 located at an end of the bottom wall 116 which helps retain the suture on the suture spool. The spool may be configured so that it fits snugly within the channel 112 and rotates smoothly to easily feed the suture to the needle during a suturing procedure.

The spool may be configured to facilitate winding and/or unwinding of the suture. In one illustrative embodiment shown in FIG. 9, the bottom wall surface 118 is tapered at an angle $A_1$ relative to the axis of rotation 110 to facilitate uniform winding of the suture 104 onto the suture spool. The bottom wall surface 118 may be angled so that it rises away from the axis of rotation 110 in a direction from a proximal end 122 of the spool to the distal end 124 of the spool. This arrangement may also help reduce drag and facilitate smooth unwinding of the suture from the spool as the suture is drawn in the distal direction during a suturing procedure. In this regard, the angle of the bottom wall surface helps lift and direct the suture from the spool as the suture is pulled distally across the spool.

Figure 9:
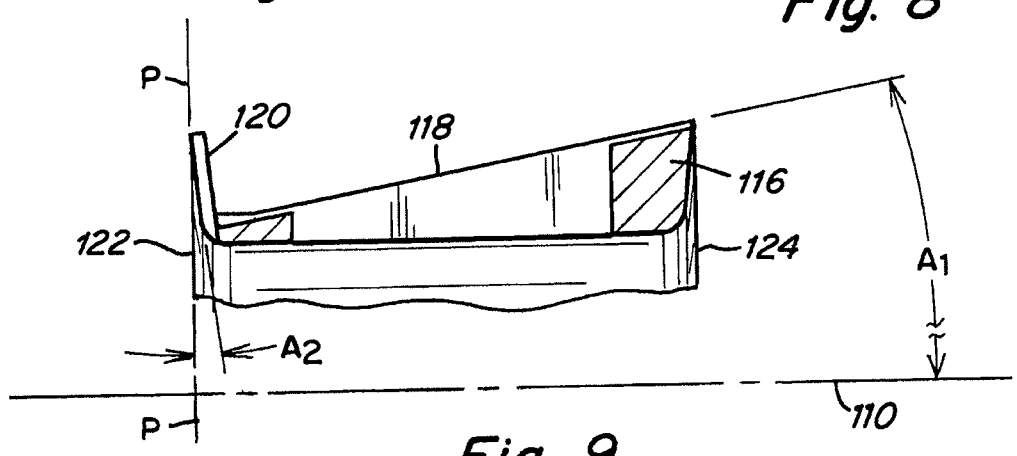
FIG. 9 is an enlarged partial view of the suture spool taken along detail line 9-9 of FIG. 8.

It may be desirable to reduce potential gaps or spaces between the spool and the channel within which the suture material could potentially become pinched or snagged as it is wound or unwound from the spool. In one illustrative embodiment, the end wall 120 is configured to urge the suture spool 102 in an axial direction along the axis of rotation 110. As shown in FIG. 9, the end wall 120 may be angled so that it exerts a biasing force against one side 117 of the channel 112 (FIGS. 3-4) to urge the spool in the axial direction and against the opposite side 119 of the channel. This arrangement may help close up potential gaps or spaces between the spool and the channel that could otherwise catch or snag the suture.

The end wall 120 may be configured as a flexible or resilient member that exerts a spring-like force for urging the spool in the axial direction. In one illustrative embodiment shown in FIG. 9, the end wall 120 is oriented at an angle $A_2$ that is non-perpendicular to the axis of rotation 110 to drive the spool away from the side of the channel contacted by the end wall. As shown, the end wall 120 may be located at the proximal end 122 of the bottom wall to bias the spool in the distal direction. If desired, the end wall may be configured so that only a portion of the wall is angled.

In one illustrative embodiment, the end wall 120 has a thickness of approximately 0.008 inches and is oriented at an angle $A_2$ of approximately 6° from a plane P perpendicular to the axis of rotation 110. In another illustrative embodiment, the end wall is oriented at an angle $A_2$ of at least 3°. In a further illustrative embodiment, the end wall is oriented at an angle $A_2$ of at least 5°. In another illustrative embodiment, the end wall is oriented at an angle $A_2$ of approximately 5° to 7°. The angle $A_2$ may be varied to provide a desired biasing force while limiting the drag or friction forces on the spool.

In one illustrative embodiment, the bottom wall 116 is oriented at an angle $A_1$ of approximately 11° from the axis of rotation 110. In another illustrative embodiment, the bottom wall is oriented at an angle $A_1$ of at least 5°. In a further illustrative embodiment, the bottom wall is oriented at an angle $A_1$ of at least 10°. In another illustrative embodiment, the bottom wall is oriented at an angle $A_1$ of at least 12°.

In one illustrative embodiment, the spool 102 has a width $W_1$ (FIG. 8) of approximately 0.299 inches and the spool channel 112 has a width $W_2$ (FIG. 3) of approximately 0.300 inches. The spool has an inner diameter $D_1$ (FIG. 8) of approximately 0.81 inches and the spool channel has an outer diameter $D_2$ (FIG. 3) of approximately 0.79 inches. The spool is molded from a plastic material, such as polypropylene.

Figure 6:
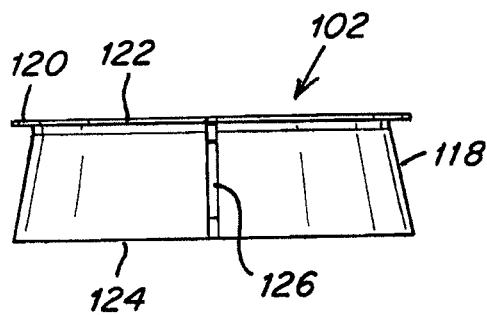
FIG. 6 is a top plan view of the suture spool of FIG. 5.
Figure 7:
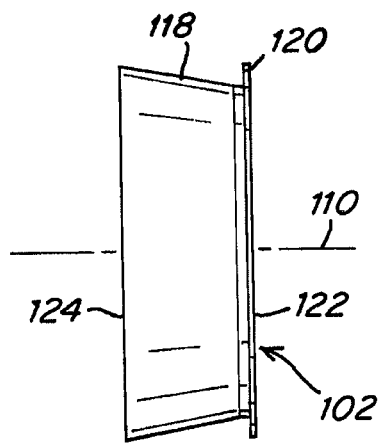
FIG. 7 is a side elevation view of the suture spool of FIG. 5.
Figure 8:
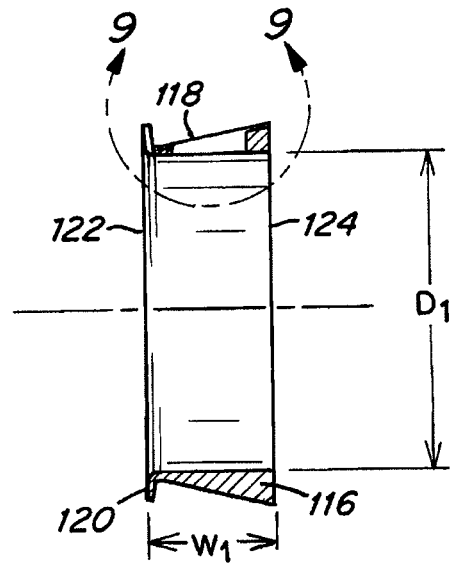
FIG. 8 is a cross-sectional view of the suture spool taken along section line 8-8 of FIG. 5.

The illustrative arrangement allows the suture spool 102 to rotate smoothly within the channel 112 with relatively low friction so that the suture 104 may be drawn from the spool with a light force. As shown in FIG. 6, the spool 102 may include a gap 126 that allows the spool to be opened and placed in the channel about the handle. However, it is to be appreciated that the spool may be provided in other configurations and fabricated from other materials as would be apparent to one of skill in the art.

The control handle may be configured to allow access to at least a portion of the suture so that a user may, if desired, place tension on the suture during a suturing procedure and/or pay out a length of suture from the spool. In one illustrative embodiment shown in FIGS. 3 and 10-11, the control handle 100 includes a suture access cavity 130 that provides external access to a length of suture 104 that may be grasped and manipulated by a user. As shown, the suture 104 passes through the cavity 130 as it travels from the spool 102 to the needle (not shown). The suture 104 is spaced above the bottom wall of the cavity 130 so that the suture may be more easily grasped by the user.

As shown, the cavity 130 is located distal to the suture spool 102 to receive suture being fed to the needle from the spool in the distal direction. If desired, one or more additional suture access cavities may be provided on the control handle. It is also to be appreciated that suture access is not required with each embodiment of the suturing device.

The control handle 100 may be configured to facilitate passage and routing of the suture from the spool to the needle. In one illustrative embodiment shown in FIG. 3, the handle includes a suture passage 132 that extends from the spool channel 112 to one end of the suture access cavity 130 to direct the suture 104 from the spool to the access cavity. As shown, the passage 132 may be an open channel that extends across the surface of the handle. The passage 132 may be oriented at an angle $A_3$ relative to the spool channel 112 that helps reduce drag on the suture material as it passes from the spool to the access cavity. After crossing the access cavity 130, the suture 104 passes through an opening 134 at the opposite end of the cavity and along one or more interior passages 114 (FIG. 4) that extend along the distal portion of the handle. Upon exiting the handle, the suture extends along the length of the suturing device to the needle (not shown).

In one illustrative embodiment, the suture passage 132 is oriented at an angle $A_3$ of approximately 19° relative to the distal side 119 of the spool channel. The suture passage 132 has a width $W_3$ of approximately 0.031 inches to receive and guide the suture. In another illustrative embodiment, the suture passage is oriented at an angle $A_3$ of 25° or less. In a further illustrative embodiment, the suture passage is oriented at an angle $A_3$ of 20° or less. In another illustrative embodiment, the suture passage is oriented at an angle $A_3$ of 18° or less. However, it is to be appreciated that the suture passage, if even desired, may be provided in other configurations as would be apparent to one of skill in the art.

As described above, the spool 102 is located in an annular channel 112 that extends about the circumference of the handle. A cover may be provided on the control handle to cover and help manage and/or protect the suture. In one illustrative embodiment shown in FIGS. 10-14, the cover 140 is configured to overlie the annular spool channel 112 provided in the control handle. The cover 140 includes an annular body 142 having a thin-walled tubular shape. The cover is configured to be slid onto the control handle and over the spool channel.

Figure 10:
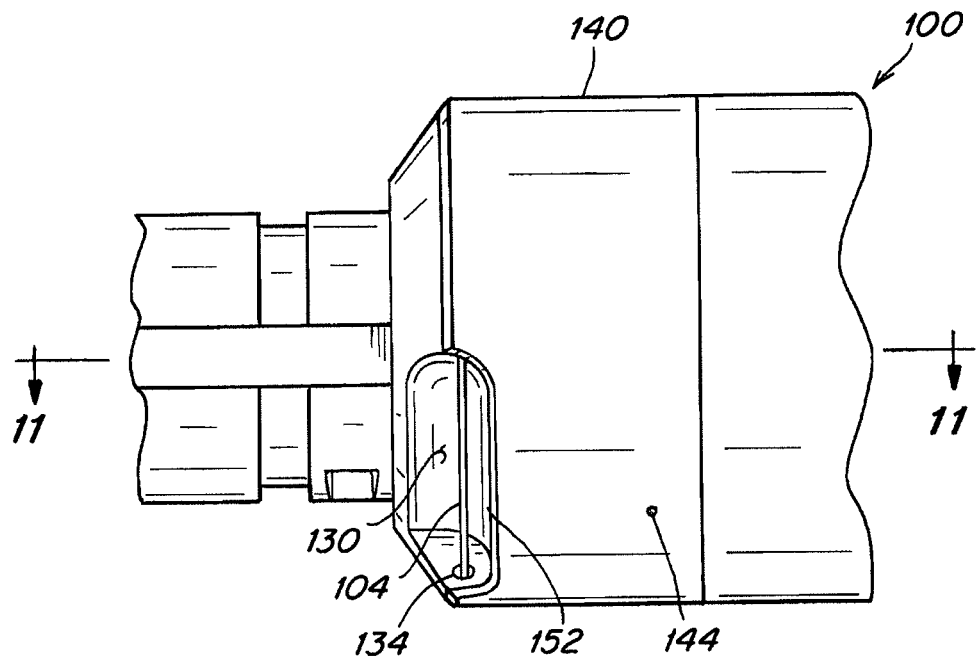
FIG. 10 is the enlarged plan view of FIG. 3 illustrating a cover provided over the suture spool channel according to one illustrative embodiment.
Figure 12:
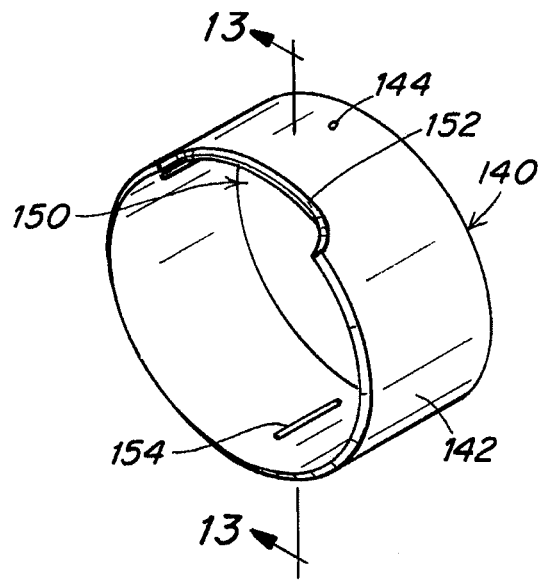
FIG. 12 is a perspective view of a suture spool cover according to one illustrative embodiment.
Figure 13:
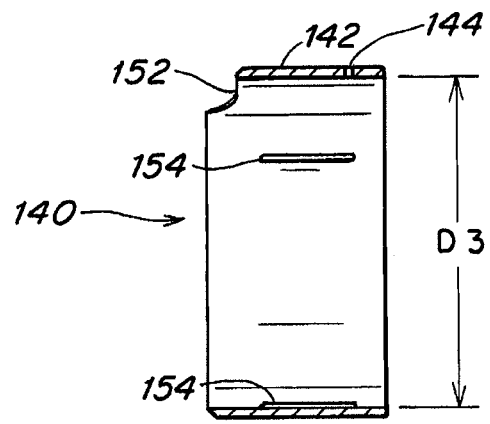
FIG. 13 is a cross-sectional view of the cover taken along section line 13-13 of FIG. 12.
Figure 14:
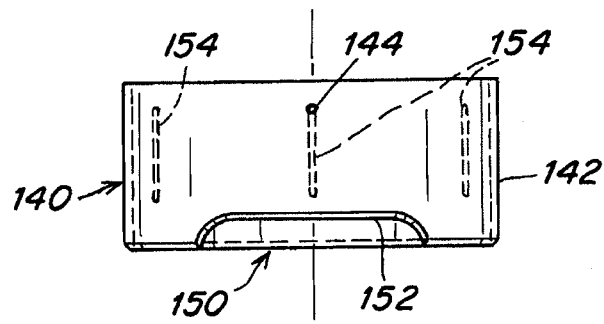
FIG. 14 is a top plan view of the cover of FIG. 12.

The cover 140 may be configured to facilitate winding suture onto the spool. In one illustrative embodiment, the cover is rotatably supported on the control handle independent of the spool so that suture material can be coupled to the cover and wound onto the spool by rotating the cover relative to the spool. As shown in FIGS. 10 and 12, the cover 140 is provided with an opening 144 that is adapted to receive suture material therethrough for coupling the suture to the cover and winding the suture onto the spool. As shown, the opening 144 is located on a portion of the cover wall that overlies the spool when the cover is fully installed on the handle.

One illustrative embodiment of a procedure for loading suture onto the suture spool will be described in connection with FIGS. 15-21.

Figure 15:
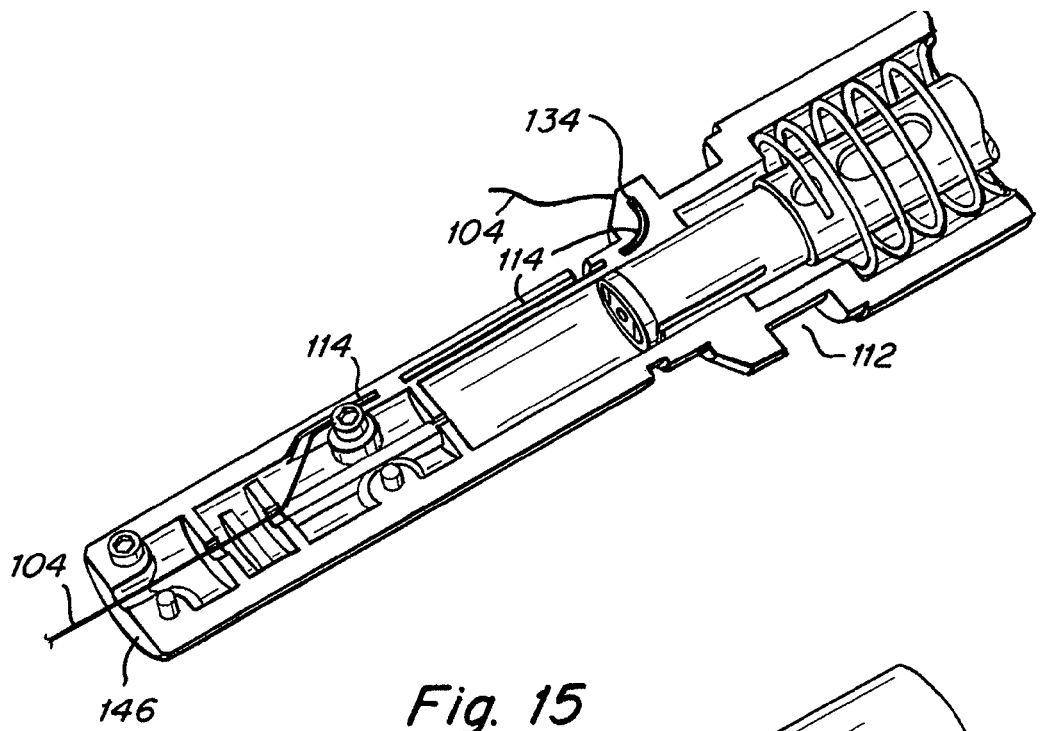
FIGS. 15-21 are schematic views of the control handle illustrating a procedure for loading suture onto the control handle according to one illustrative embodiment.
Figure 16:
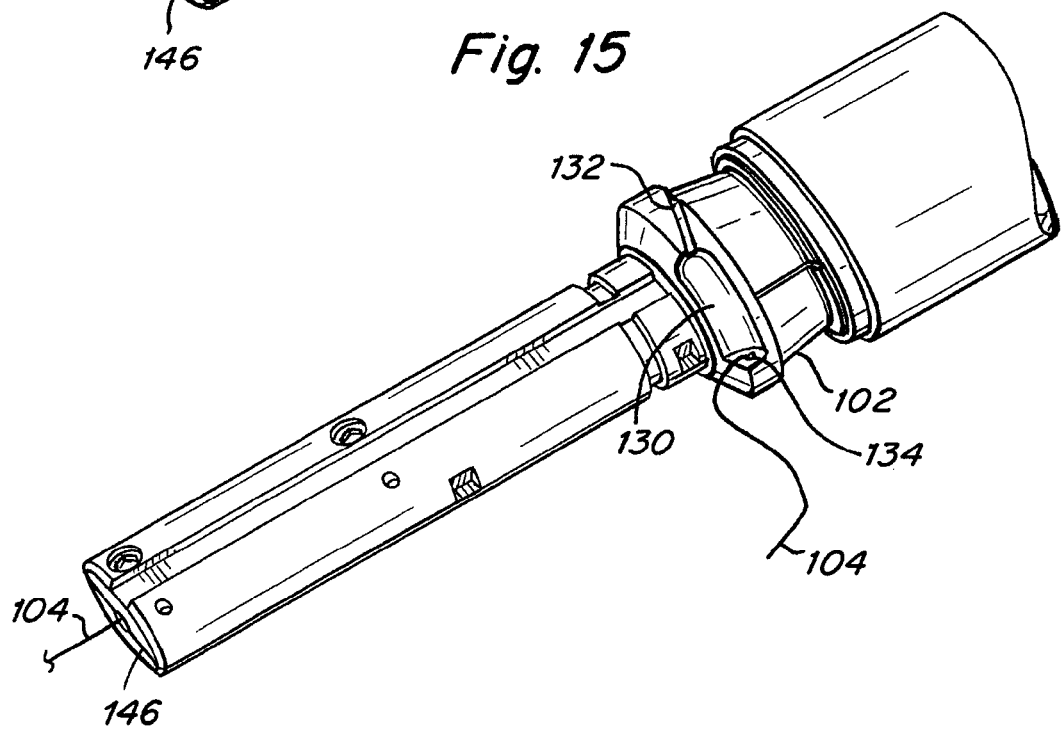

As shown in FIGS. 15-16, the suture 104 is threaded through the shaft (not shown) of the suturing device and into the distal end 146 of the handle. The suture 104 continues along the internal passages 114 of the handle and through the opening 134 into the suture access cavity 130. As shown in FIG. 15, the handle housing is initially separated to facilitate threading of the suture 104 through the handle. Once threaded through the suture access cavity opening 134, the housing is fully assembled and the suture spool 102 is positioned about the housing in the spool channel 112 as shown in FIG. 16.

Figure 17:
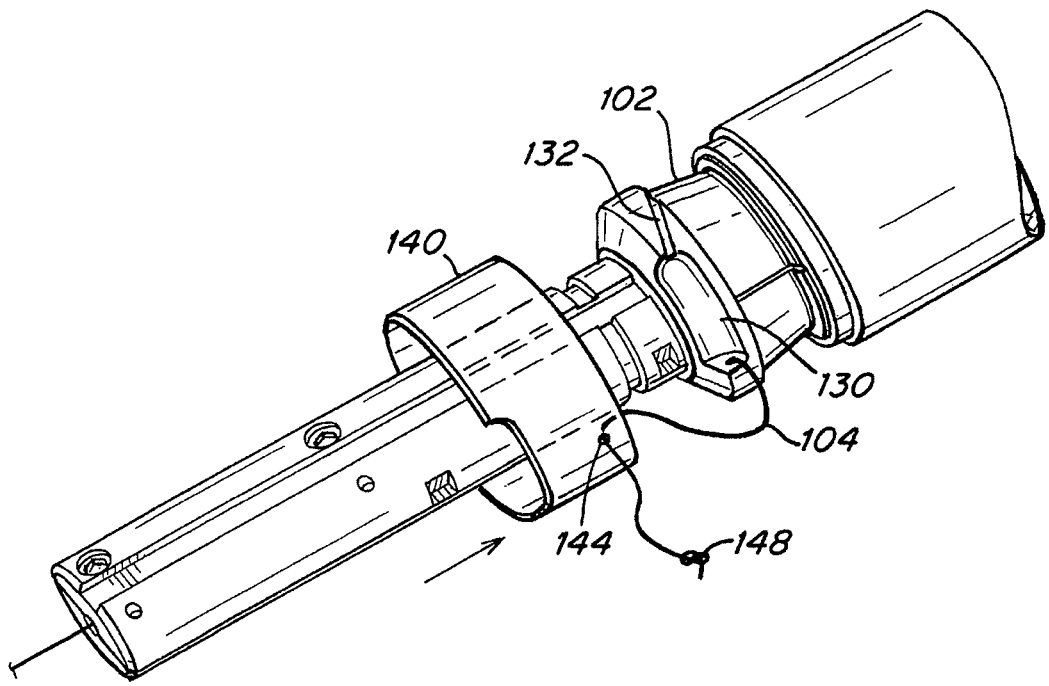

As shown in FIG. 17, with the suture spool 102 positioned within the spool channel 112, the suture 104 is threaded through the opening 144 in the cover 140 and tied with a knot 148 to secure the suture to the cover.

Figure 18:
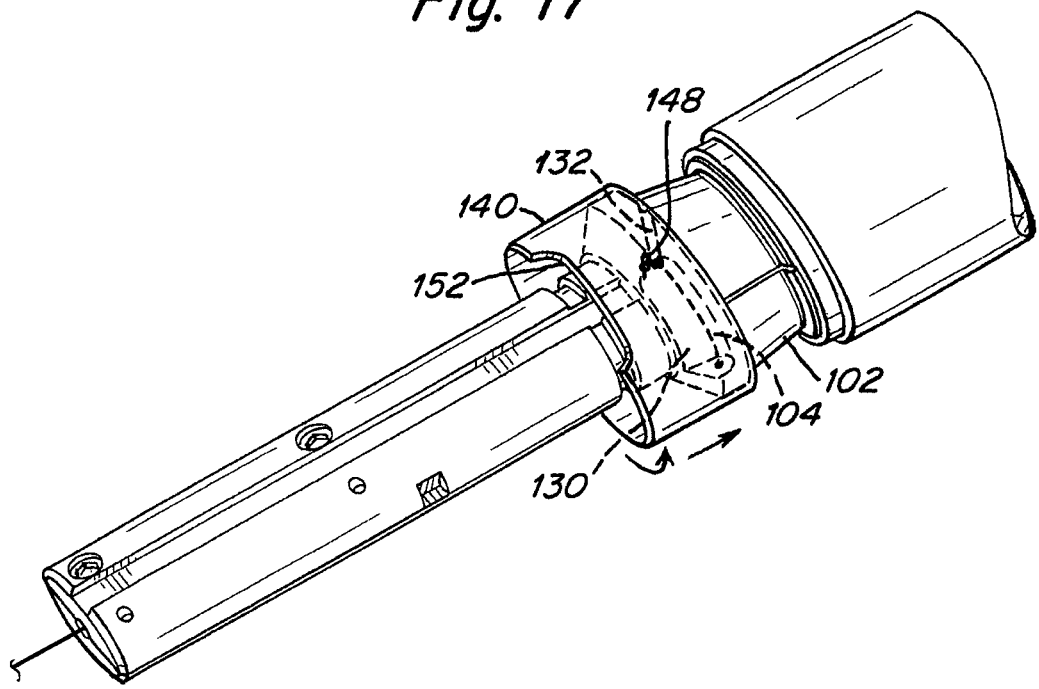

As shown in FIG. 18, with slack being removed from the suture, the cover 140 is pushed onto the handle and rotated to draw the suture 104 across the access cavity 130 and align the suture with the end of the suture passage at the access cavity.

Figure 19:
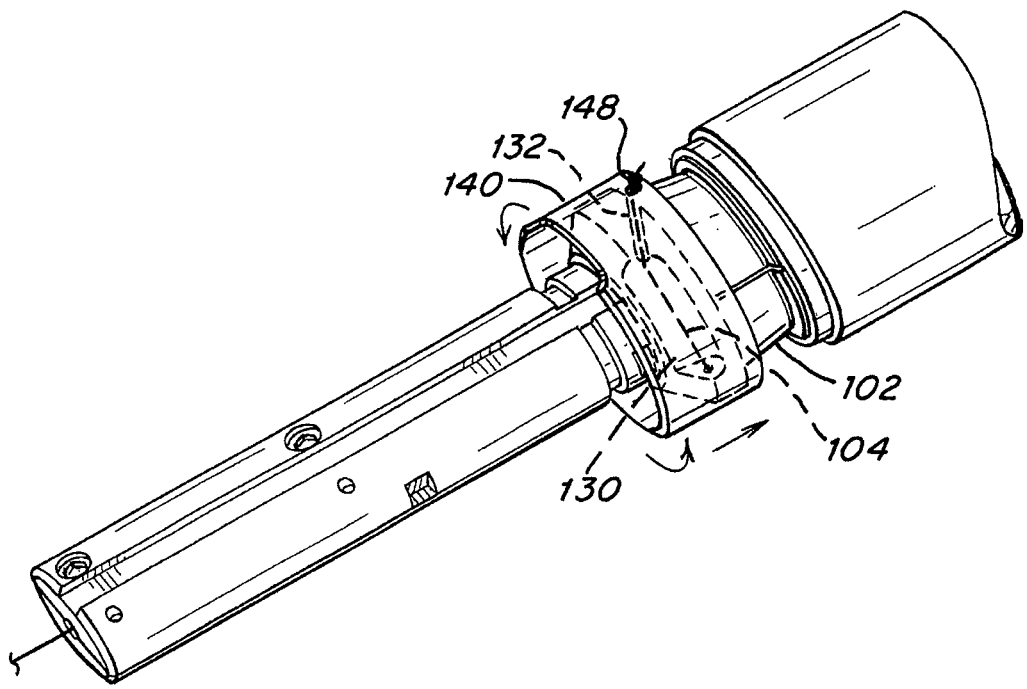
Figure 20:
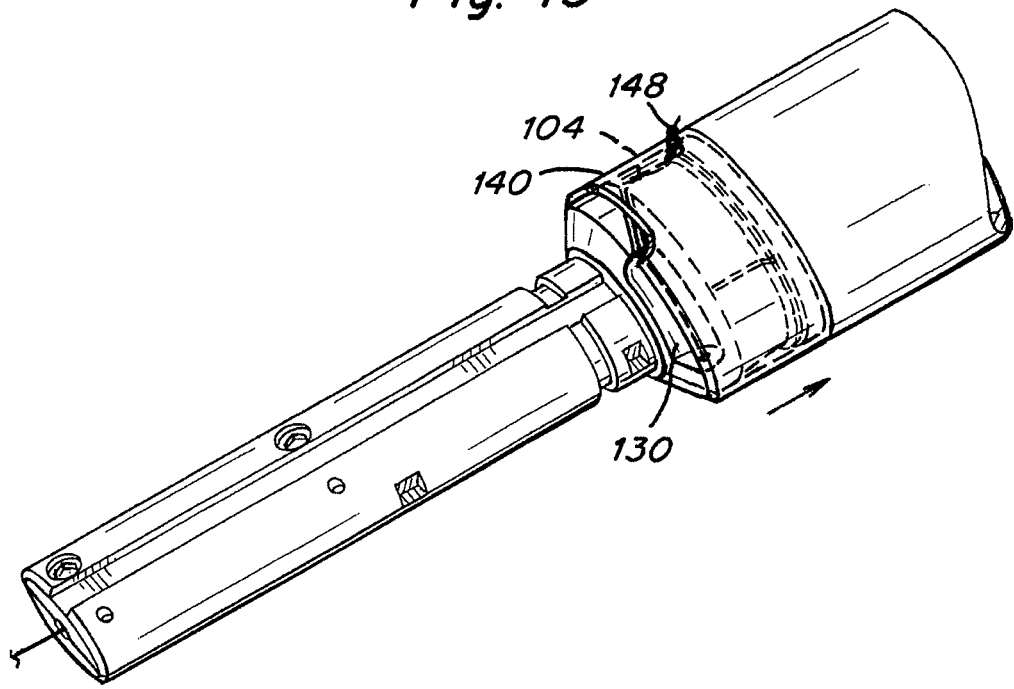

As shown in FIG. 19, the cover 140 is rotated and pushed further onto the handle to feed the suture 104 into and through the suture passage 132. After the suture is fed through the passage, the cover 140 is pushed fully onto the handle to completely cover the suture spool channel 112 as shown in FIG. 20.

Figure 11:
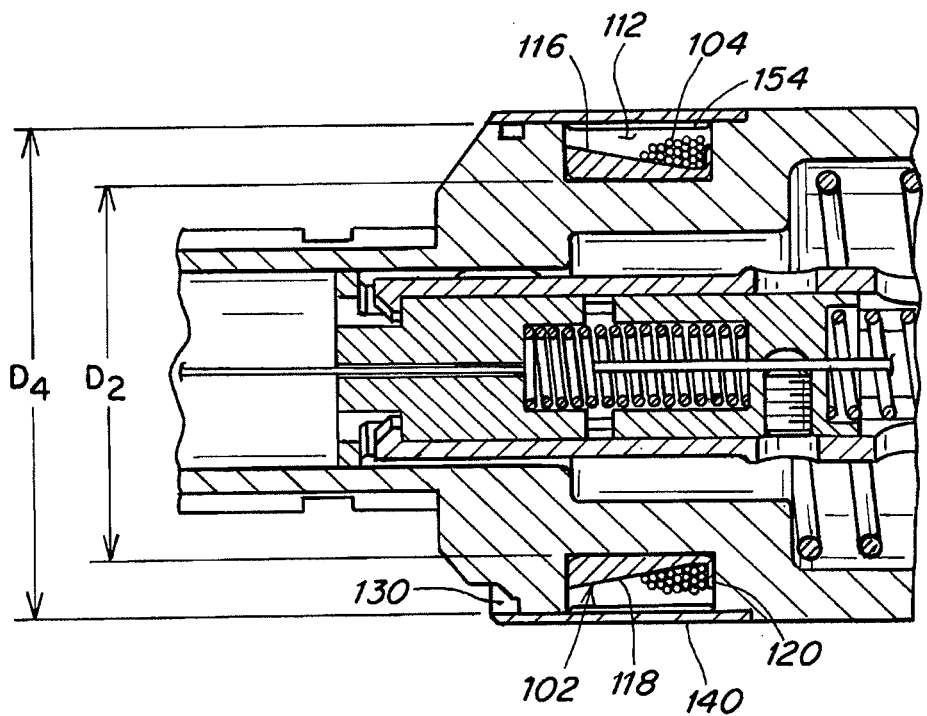
FIG. 11 is a cross-sectional view taken along section line 11-11 of FIG. 10 illustrating the suture management arrangement according to one illustrative embodiment.
Figure 21:
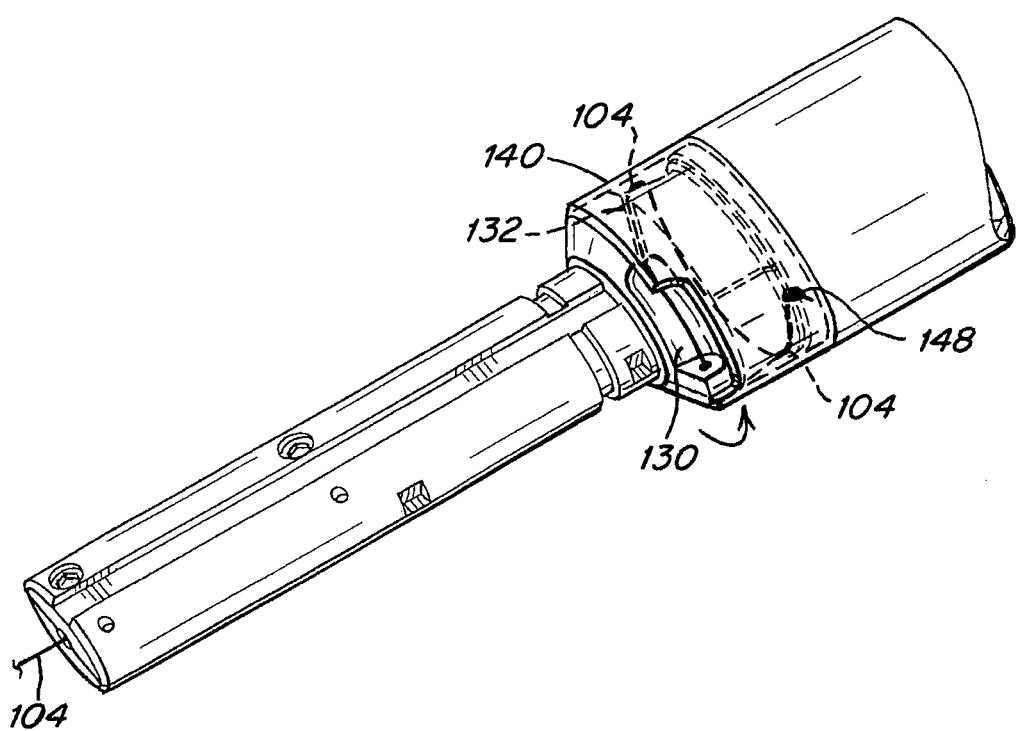

With the cover 140 positioned over the spool 102, it is rotated to load the suture onto the spool. As shown in FIG. 21, the suture opening 144 in the cover 140 is positioned over the proximal end 122 of the suture spool 102 so that suture is initially wound onto the proximal end of the spool. As the cover is rotated, the suture builds up on the proximal end 122 of the spool, as shown in FIG. 11, and eventually builds up toward the distal end 124 of the spool due to the tapered configuration of the bottom wall of the spool.

When the spool is fully loaded, or otherwise loaded with a desired amount of suture, the knot 148 is removed from the end of the suture 104 passing through the cover 140. This decouples the suture from the cover so that the spool may rotate independent of the cover and allow the suture to be easily drawn from the spool.

Having described one illustrative procedure for loading suture onto the spool, it is to be understood that other suture loading procedures are contemplated as would apparent to one of skill in the art.

The cover 140 may be configured to allow access to the suture access cavity 130 when oriented in a first position and to cover the suture access cavity 130 when oriented in a second position. In one illustrative embodiment shown in FIGS. 12-14, the cover 140 includes an access region 150 that corresponds to the cavity configuration so that the cavity 130 is uncovered and becomes accessible when the cover is rotated to the first position to align the access region with the cavity. As shown, the access region 150 may be formed by a notch or opening 152 provided along the distal edge of the cover body. The cover has a length that overlies and covers the access cavity when the cover is rotated to a second position in which the notch is no longer aligned with the cavity.

The cover may include one or more securement features that are configured to maintain the cover in position on the handle. In one illustrative embodiment shown in FIGS. 12-14, the cover 140 includes one or more internal ribs 154 that cooperate with the spool channel 112 to help hold the cover in position over the channel. As shown, the ribs 154 extend across the width of the cover and have a length that fits closely within the channel.

In one illustrative embodiment, the cover body 142 has an inner diameter $D_3$ of approximately 1.054 inches and includes three inner ribs 154 with a height of approximately 0.010 inches each, resulting in the cover having an effective inner diameter of approximately 1.044 inches. The control handle has a diameter $D_4$ (FIGS. 3 and 11) of approximately 1.050 inches adjacent the spool channel 112. The ribs 154 have a length L of approximately 0.28 inches so that they extend across and fit within the width of the spool channel when the cover is positioned fully over the channel to help maintain the cover in its desired position. However, it is to be appreciated that the cover may be provided in other configurations and employ other securement features as would be apparent to one of skill in the art.

Suturing Head

Figure 22:
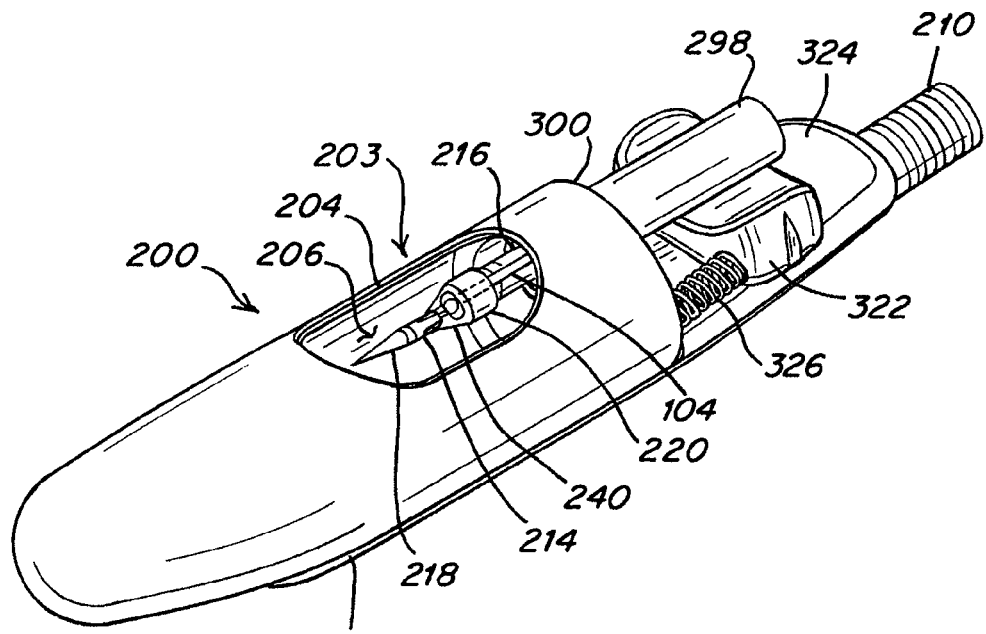
FIG. 22 is a perspective view of a suturing capsule according to one illustrative embodiment of the suturing device of FIG. 1.
Figure 23:
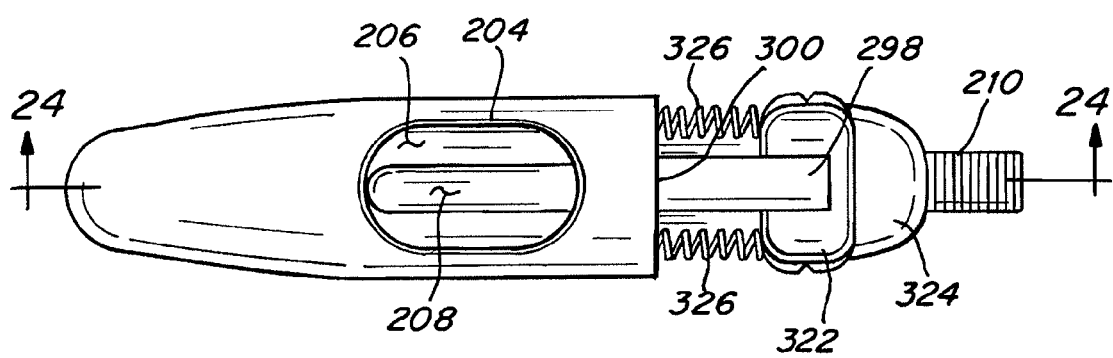
FIG. 23 is a top plan view of the suturing capsule of FIG. 22.
Figure 24:
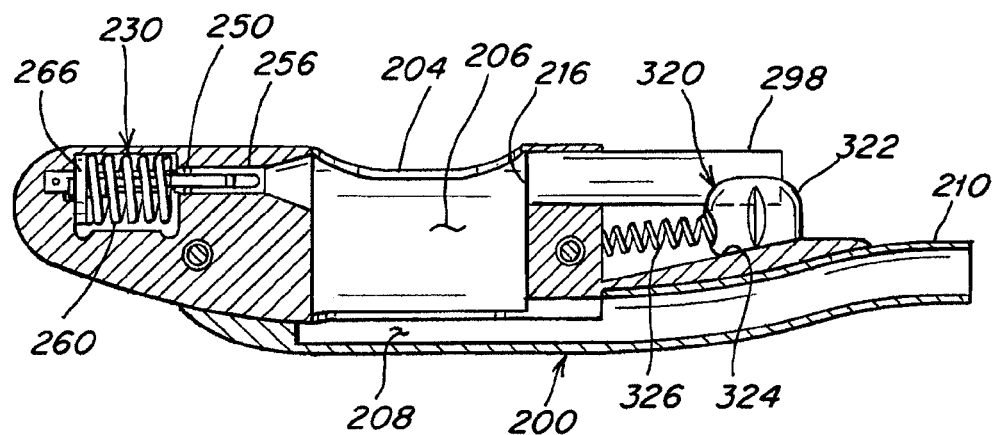
FIG. 24 is a cross sectional view of the suturing capsule taken along section line 24-24 of FIG. 23.

In one illustrative embodiment shown in FIGS. 22-24, the suturing head 200 includes a capsule 202 having an atraumatic shape to reduce the chance of trauma to internal tissues during an endoscopic suturing procedure. The capsule is similar in configuration and operation to a capsule disclosed in U.S. Pat. Publication 2005/0033319, which is incorporated herein by reference.

The capsule may include a tissue capture region 203 that is configured to capture tissue. In one illustrative embodiment, the capsule includes a suction port 204 that opens to a tissue suction chamber 106 into which tissue portions to be sutured may be collected via a vacuum introduced into the chamber. As shown in FIG. 23, an elongated channel 208 is provided at the bottom of the suction chamber for introducing negative pressure (i.e., vacuum) to the suction chamber 206 to selectively capture a tissue portion that is to be sutured. The vacuum is introduced to the channel 108 through vacuum tube 210 extending proximally from the capsule 100 and joined to a separate vacuum line 212 (FIG. 1) that extends along the exterior of the endoscope.

The capsule is configured to receive a needle 214 that is slidable through a needle track 216 formed through the capsule. The needle may include a solid shaft with a sharpened distal tip 218 that is joined at its proximal end to a pusher shaft (not shown) that extends proximally from the suture capsule, through the working channel of the endoscope. When the needle is moved longitudinally through the needle track, it passes through and traverses the suction chamber 206 so that tissue suctioned into the chamber will be penetrated by the distally advancing needle.

The pusher shaft exits the proximal end of the endoscope where it may be joined to and manipulated by the control handle 100. One example of a control handle mechanism that may be particularly suited for use with the suturing device is disclosed in US 2005/0033319. However, it is to be appreciated that other suitable control handles may be employed as would be apparent to one of skill in the art.

The needle may be employed to place a suture through tissue drawn into the suction chamber. In one illustrative embodiment shown in FIG. 22, the needle 214 carries an annular suture tag 220 that fits closely about the outside surface of the needle. A suture 104 is joined to the suture tag to be carried through a suctioned tissue portion when the needle carrying the suture tag is advanced distally. The suturing device may be configured to selectively secure and release the suture tag to and from the needle.

The suturing device may be configured so that full distal advancement of the needle places the suture tag 220 within a suture tag catch 230 located distal to the suction chamber. After penetrating a captured tissue portion and entering the suture catch, the suture tag 220 may be released and the needle withdrawn proximally leaving behind the suture tag in the suture tag catch.

The suture tag catch 230 may be configured to release the suture by moving the catch a predetermined distance in the longitudinal direction. The suture tag catch 230 may also be configured so that movement of the catch to release the suture tag requires the application of a predetermined axial force to the catch.

Figure 25:
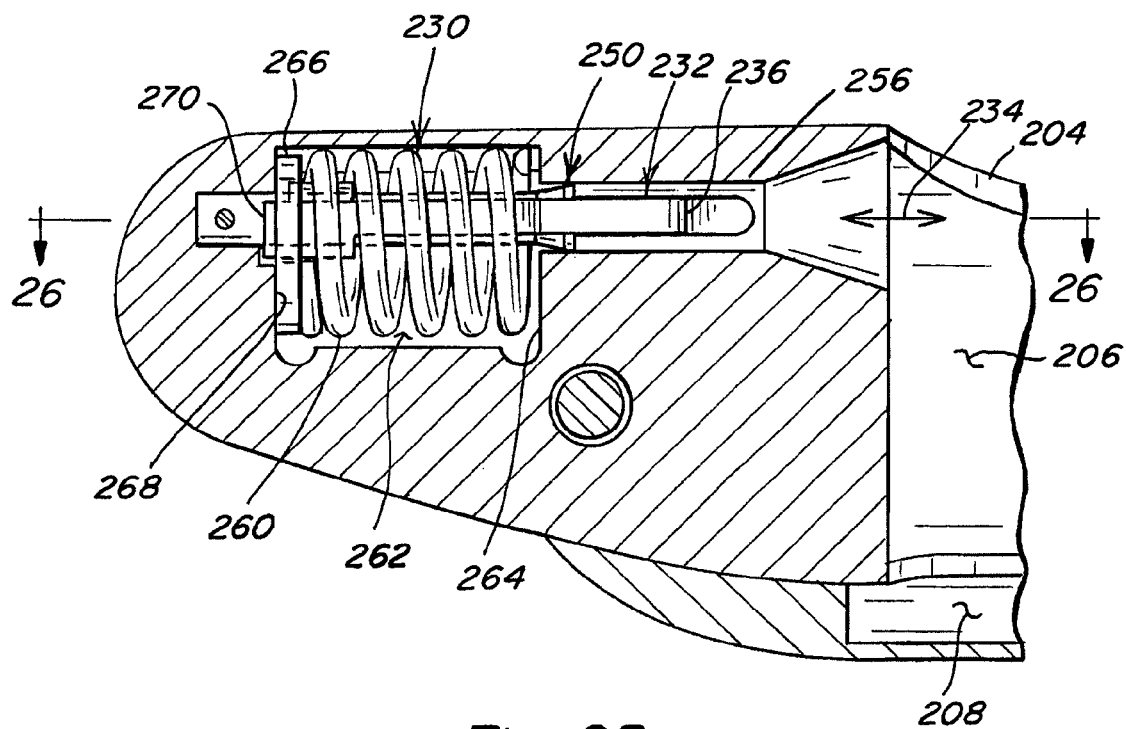
FIG. 25 is an enlarged view of a suture tag catch according to one illustrative embodiment employed with the suturing capsule of FIGS. 22-24.
Figure 26:
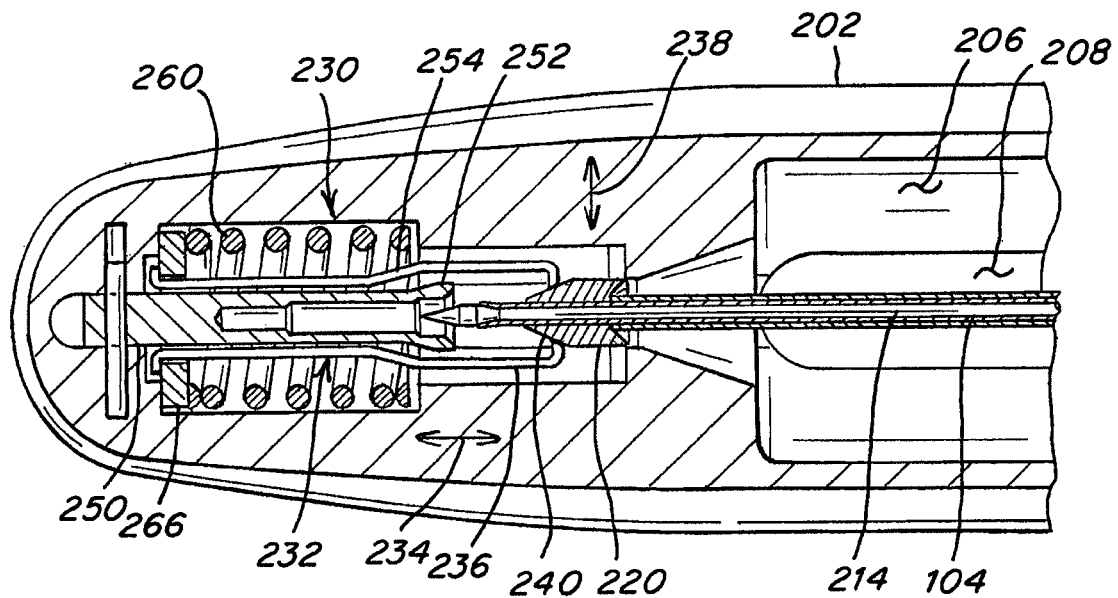
FIG. 26 is a cross sectional view of the suture tag catch taken along section line 26-26 of FIG. 25 illustrating the needle being extended distally toward the catch.

In one illustrative embodiment shown in FIGS. 24-26, the suture tag catch 230 includes a tag locking clip 232 that is movable in the longitudinal direction 234. The locking clip 232 includes a plurality of fingers 236 that are movable between a closed or locked position to secure the suture tag and an open or unlocked position to release the suture tag from the catch. The locking clip may employ resilient fingers 236 that are self-biasing inwardly in a lateral or radial direction 238 (FIG. 26) to the closed or locked position to secure the suture tag within the catch. In this manner, the fingers are movable in both the longitudinal and lateral directions to secure and release the suture tag.

Figure 27:
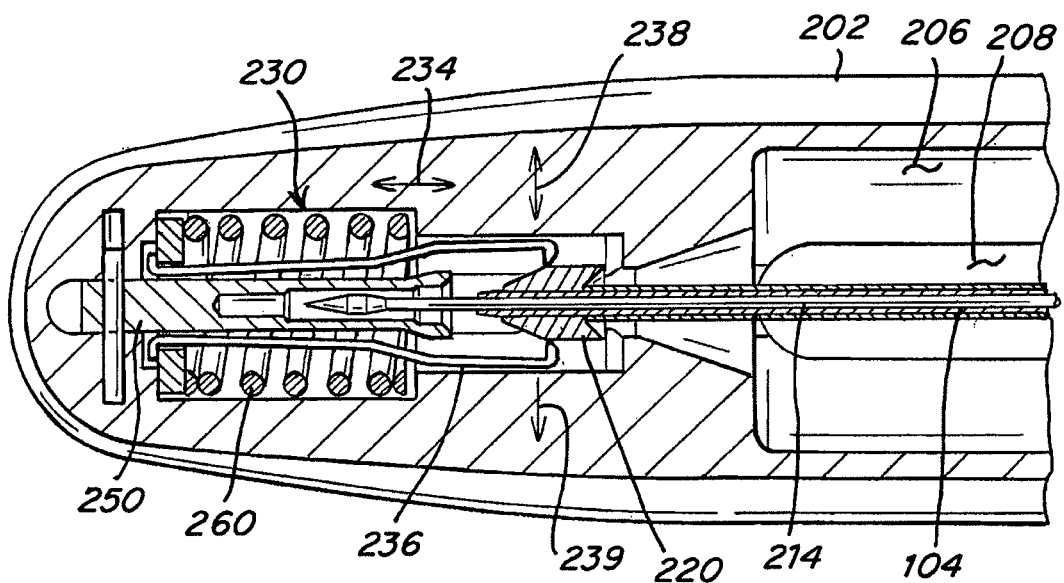
FIG. 27 illustrates the suture tag expanding the suture tag clip to an open position as the needle is extended further into the suture tag catch.

One or both of the suture tag and the tag locking clip may be configured to facilitate insertion of the suture tag into the catch. In one illustrative embodiment shown in FIGS. 26-27, the suture tag 220 has a tapered or conically shaped distal end portion 240 that expands the locking fingers 236 outwardly (illustrated by arrow 239) as the needle and the suture tag are extended in the distal direction into the catch. The tapered distal end 240 also creates a low profile that may facilitate passage of the suture tag through tissue as the needle and suture tag are advanced distally through the tissue.

Figure 28:
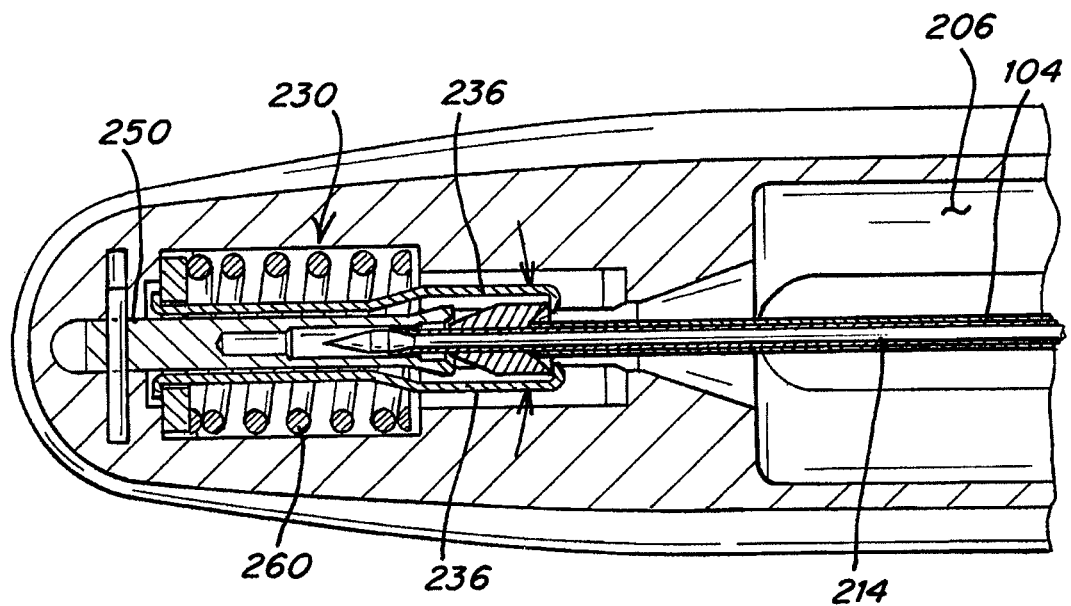
FIG. 28 illustrates the suture tag being fully advanced into the suture tag catch with the suture tag clip in a closed position to secure the suture clip.

Once the needle has been fully extended in the distal direction into the catch, the locking fingers 236 return to the closed or locked position behind the suture tag 220, as shown in FIG. 28. In this locked position, the suture tag 220 is retained by and cannot be removed from the catch until a predetermined axial force is exerted in the proximal direction to withdraw the suture tag from the catch.

Figure 29:
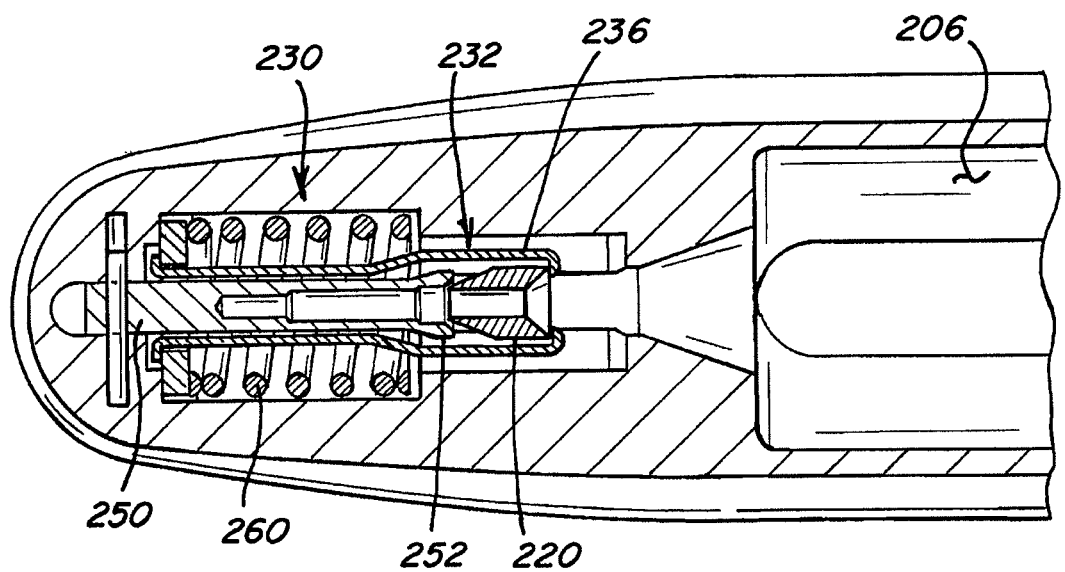
FIG. 29 illustrates the needle having been withdrawn proximally from the suture tag catch with suture tag retained by the suture tag clip.

With the suture tag 220 secured within the catch 230, the suture tag can be unlocked from the needle and the needle withdrawn across the chamber, thereby stripping the suture tag from the needle and retaining the tag at the distal end of the chamber with the catch, as shown in FIG. 29.

After capture and release of the suture tag in the suture tag catch 230, the needle may be withdrawn proximally and the tissue released from the suction chamber 206 with a suture 104 left passing through the tissue (not shown) and having one end joined to the captured suture tag 220 within the catch and the other end of the suture extending into the needle track 216, through the working channel of the endoscope and exiting the proximal end of the endoscope.

Figure 30:
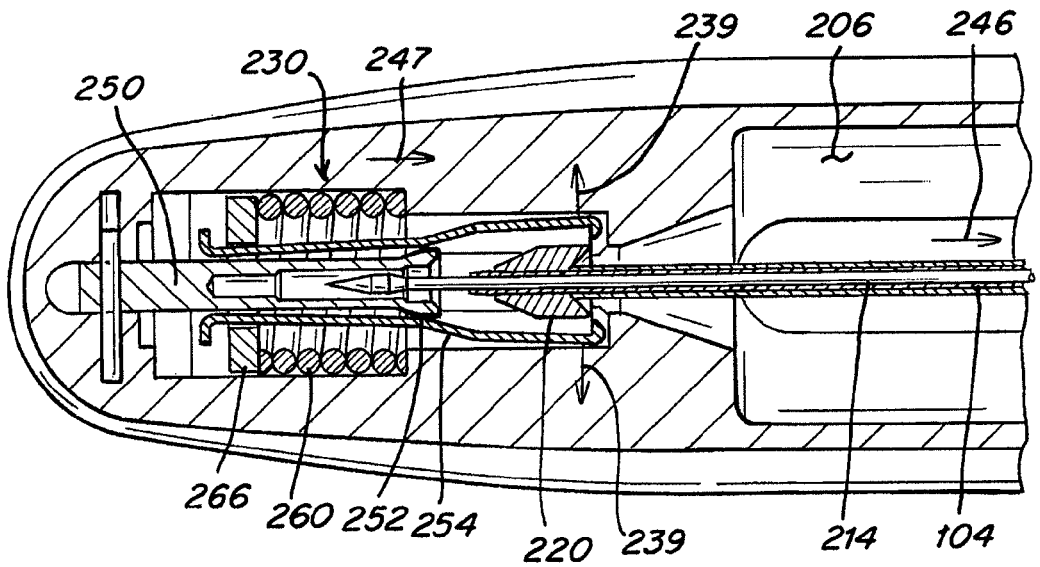
FIG. 30 illustrates the suture tag clip being drawn in the proximal direction by the needle and the suture tag with the clip being opened to release the suture tag.

To release the suture tag from the suture tag catch, the needle 214 is extended into the catch 230 and the suture tag 220 is secured to the needle. With the suture tag secured, as shown in FIG. 30, the needle can be retracted in the proximal direction 246 causing the tag locking clip 232, which is gripping the secured suture tag, to similarly move in the proximal direction 247. The suture tag catch 230 may be configured so that drawing the tag locking clip 232 in the proximal direction opens the locking fingers to release the suture tag 220 from the catch.

In one illustrative embodiment, the suture tag catch 230 employs a cam arrangement to open the tag locking clip. The cam arrangement includes a cam tube 250 with an external cam surface 252 that co-acts with a cam follower 254 provided on each of the locking fingers 236 to expand the locking clip to an open position once the locking clip is drawn a predetermined distance in the proximal direction. The cam surface 252 is located at the proximal end of the tube and tapers outwardly in the proximal direction to expand the locking fingers 236 as the clip is drawn in the proximal direction. The cam follower 254 includes an offset bend formed in each locking finger 236 that engages and interacts with the cam surface 252 of the tube to spread open the fingers of the locking clip. Similar to the cam surface, the offset bend 254 is angled outwardly in the proximal direction.

In one embodiment, the cam surface has a taper of approximately 15° and the cam follower has an offset bend angle of approximately 12°. It is to be appreciated, however, that other arrangements may be used to open the tag locking clip to release the suture tag from the catch, as would be apparent to one of skill in the art.

As shown in FIGS. 25-26, the cam tube 250 is supported within the capsule and maintained in axial alignment with the needle. The cam tube may be configured to receive at least a portion of the needle 214 therein (FIGS. 27-28) when the needle is extended into the suture tag catch. The capsule may provided with an elongated channel 256 that is aligned with and receives the needle 214 as the needle is extended across the suction chamber 206 and into the catch 230. As shown, the proximal end of the cam tube 250 is supported in the distal end of the channel 256 and the elongated fingers 236 extend in the proximal direction along a portion of the channel toward the suction chamber.

The catch may be configured so that drawing the tag locking clip the predetermined distance in the proximal direction to release the locking fingers requires a predetermined amount of force to overcome the locking force of the catch. The catch may be configured so that the grip force of the fingers is greater than the release force of the catch.

In one embodiment, the suture tag catch is configured with a release force having a range of approximately 0.75-2.0 lbs applied in a straight axial direction. Preferably, the release force is approximately 1.0 lbs. It is to be appreciated, however, that the catch may be configured to require any suitable release force as would be apparent to one of skill in the art.

It may be desirable to configure the suture tag catch so that it securely retains the suture tag as a suture attached to the tag is pulled or otherwise manipulated through tissue with the suturing device. In this regard, the suturing capsule arrangement requires a suture to pull on the suture tag at an angle relative to the axial release direction of the catch during a suturing procedure. This arrangement requires that the suture apply a relatively large force on the suture tag to generate sufficient force in the axial direction to release the tag from the catch.

Figure 31:
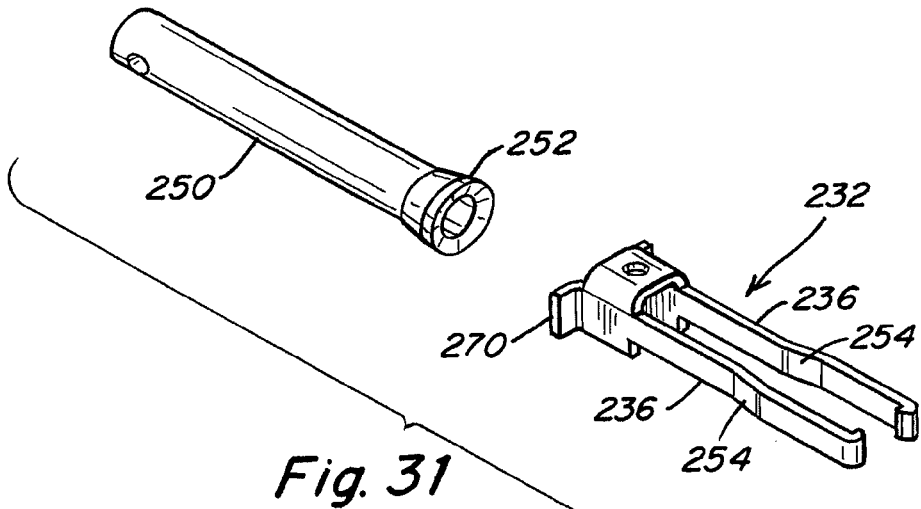
FIG. 31 is an exploded perspective view of the suture tag clip and a cam arrangement for the suture tag catch according to one illustrative embodiment.

In one illustrative embodiment shown in FIGS. 24-25, the retention force of the catch is created with a compression spring 260 that exerts a force against the base of the catch clip to bias the clip in the distal direction. As shown, the spring 260 is located within a cavity 262 of the capsule with one end of the spring engaging a proximal wall 264 of the cavity and the other end of the spring engaging a spacer 266 provided between the spring and a distal wall 268 of the cavity. As shown in FIGS. 25 and 31, the catch clip 232 includes a pair of ears 270 that engage the opposite side of the spacer 266 and pull the spacer in the proximal direction to compress the spring as the catch clip is drawn proximally by the suture tag.

In one embodiment, the suture tag catch 230 is configured so that the spring 260 applies a preload of approximately 1.9 lbs on the clip with the clip in its locked position. A clip displacement in the axial direction of approximately 0.030-0.040 inches is required to sufficiently open the clip to release the suture tag. The spring 260 is a coil spring with a spring rate of approximately 9.91 lbs/in with a free length of approximately 0.25 inches and an outer diameter of approximately 0.148 inches. The spring is formed of spring tempered stainless steel, type 316, wire having a diameter of approximately 0.016 inches. It is to be appreciated, however, that the spring may be fabricated from any suitable material and in other configurations to provide desired loading properties as would apparent to one of ordinary skill in the art.

The catch clip 232 may be formed from a sheet of hardened stainless steel, type 304, having a thickness of approximately 0.010 inches. The material has a hardness of Rockwell C 40-45. The clip is formed by bending the sheet into the desired shape. It is to be appreciated, however, that the clip may be configured in other suitable shapes and fabricated from any suitable material using other techniques as would be apparent to one of ordinary skill in the art.

As indicated above, the suturing device may be configured to selectively secure and release the suture tag to and from the needle. In one illustrative embodiment shown in FIGS. 32-33, a suture tag lock 280 releasably and selectively secures the suture tag 220 about the outside surface of the needle 214. The suture tag lock 280 is remotely operable from the proximal end of the endoscope with the control handle 100. The suture tag lock includes a locking sleeve 282 through which extends the needle. A portion of the locking sleeve may be configured to expand and contract in response to relative movement between the needle and the locking sleeve to secure and release the suture tag.

Figure 32:
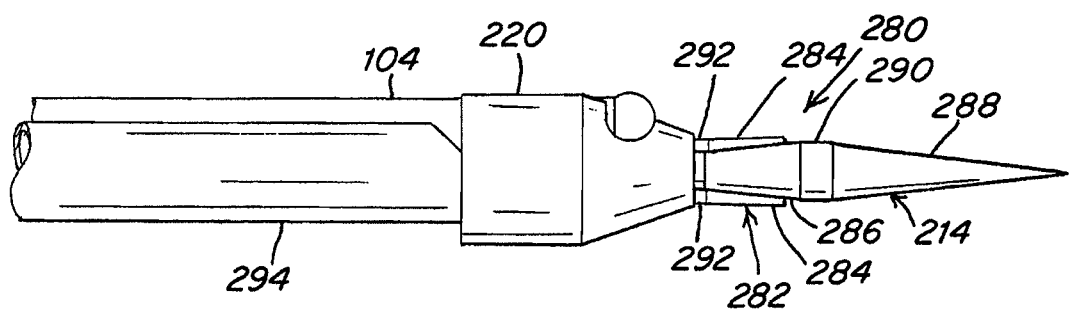
FIG. 32 is a side view of the needle with a suture tag lock according to one illustrative embodiment shown in a locked position to secure the suture tag to the needle.
Figure 33:
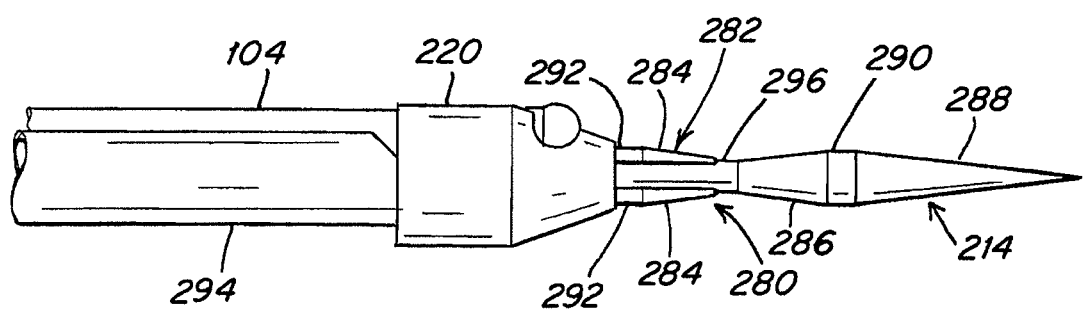
FIG. 33 illustrates the suture tag lock in an unlocked position to release the suture tag from the needle.

In one illustrative embodiment shown in FIGS. 32-33, the distal end of the locking sleeve 282 includes resilient locking splines 284 that are configured to move in a radial direction to secure and release the suture tag. As described below, the locking splines cooperate with the needle to increase and decrease the diameter of the locking sleeve relative to the through bore of the suture tag to secure and release the suture tag to and from the needle.

As shown in FIGS. 32-33, the distal end of the needle has a generally spear-like shape with a proximal increasing barrel taper 286 converging with a distal increasing barrel taper 288 to create an enlarged portion of the tip 290.

As shown in FIG. 32, when the needle is withdrawn proximally into the locking sleeve 282 of the suture tag lock, the locking splines 284 ride over the proximal barrel taper 286 of the needle 214 and expand radially outward to create locking surfaces 292 that prevent distal sliding of the suture tag 220 over the needle. The splayed splines 284 effectively increases the profile of the locking sleeve to an extent that the suture tag 220 cannot fit over it, thereby locking the suture tag in place on the needle. A stiffening sleeve 294, which has a diameter larger than the bore of the suture tag, may be provided to prevent the suture tag 220 from sliding proximally relative to the needle and the locking sleeve.

To release the suture tag so that it may slide distally relative to the needle as would be desired when leaving the tag in the suture tag catch 230 during suturing procedure, the needle 214 is moved distally relative to the locking sleeve 282. As shown in FIG. 33, movement of the needle distally relative to the locking sleeve moves the proximal barrel taper 286 away from the splines 284 so that a reduced diameter of the needle shaft 296 underlies the splines which then resiliently conform to the reduced diameter shaft. In this manner, the profile of the locking sleeve is effectively reduced to an extent that the suture tag 220 can be removed from the needle. The enlarged portion 290 of the needle, without the added thickness of the two splines 284 of the locking sleeve, has a profile over which the suture tag 220 may pass freely.

The locking sleeve 282 is slidable over the shaft of the needle 214. In one embodiment, the locking sleeve is a stainless steel hypotube having an inner diameter of approximately 0.016 inch sized to fit closely over the outside surface of the needle shaft, which has a diameter of approximately 0.0155 inch. It is to be understood that other suture tag lock arrangements are contemplated and may be employed as would be apparent to one of skill in the art.

As indicated above, the capsule may be joined to the distal end of an endoscope. In one illustrative embodiment shown in FIGS. 22-24, the capsule 200 includes a proximally extending guide tube 298 that is inserted into the working channel of the endoscope. The guide tube 298 is rigid and extends proximally from the proximal end 300 of the capsule to protrude a short distance into the working channel of the endoscope. The guide tube is open to receive the needle during operation.

Figure 34:
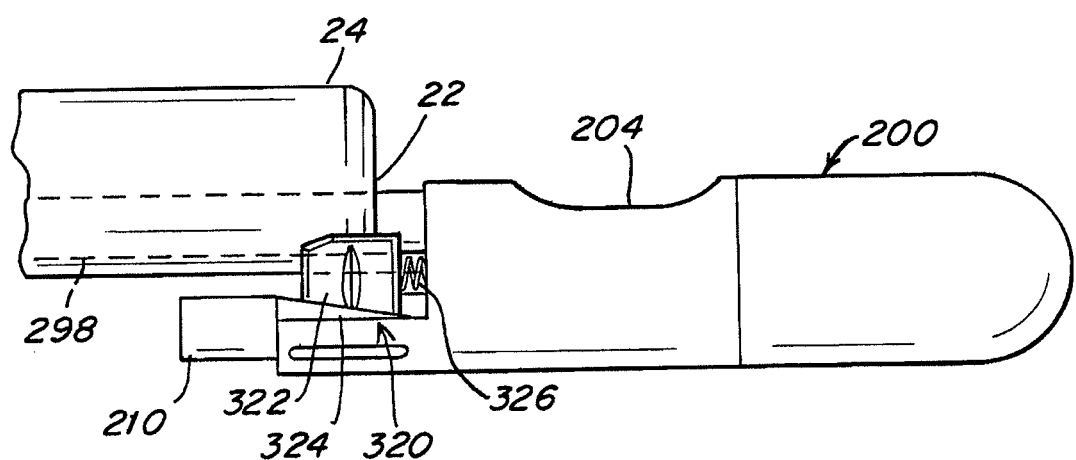
FIG. 34 is a side view of the suturing capsule of FIGS. 22-24 mounted to the distal end of an endoscope.

In one illustrative embodiment shown in FIG. 34, the capsule may be secured to the distal end of the endoscope with a reverse wedge securement mechanism. A reverse wedge and an endoscopic accessory securement mechanism is fully described in U.S. Pat. No. 6,869,395, issued Mar. 22, 2005, and titled "Endoscopic Accessory Attachment Mechanism", which is incorporated herein by reference in its entirety.

The reverse wedge securement mechanism 320 includes a wedge 322 that is slidable along an angled ramp 324 to become wedged between the distal end 22 of the endoscope 24 and the ramp surface as it slides up the ramp 324. Leverage against the distal end of the endoscope is maintained by the presence of the guide tube 298 through the working channel. One or more return springs 326 maintain force against the wedge 322 to bias the wedge upward along the ramp 324 and maintain wedge contact with the endoscope. It is to be appreciated that the capsule may be secured to an endoscope using other suitable arrangements apparent to one of skill in the art.

In one embodiment, the suture capsule may be fabricated from a rigid material, such as stainless steel. It is to be understood, however, that the capsule may be fabricated from other suitable materials apparent to one of skill in the art.

As indicated above, the suturing device may be employed with any of various conventional endoscopes. As would be understood by one of ordinary skill in the art, an endoscope conventionally includes a working channel and a viewing channel that extend along the length of the elongated shaft of the endoscope. An endoscope may also include other channels that can be used for a light source or a liquid cleaning source.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An endoscopic tissue suturing device, comprising:
 a suturing capsule that is mountable to a distal end of an endoscope, the suturing capsule including a tissue suction chamber that is adapted to capture tissue therein when a vacuum is applied thereto;
 a needle movable within the suturing capsule along a pathway that extends through the tissue suction chamber, the needle adapted to penetrate tissue captured within the tissue suction chamber when the needle is extended in a distal direction from a proximal end to a distal end of the suturing capsule;
 a control handle that is mountable to a proximal end of the endoscope, the control handle being coupled to the needle and constructed and arranged to control movement of the needle within the suturing capsule;
 a suture supply supported by the control handle, the suture supply including a length of suture that is coupled to the needle to form one or more stitches in tissue, the suture supply includes a suture spool that is rotatably supported within the control handle about an axis of rotation, the suture being unwound from the suture spool as the needle places stitches through tissue; and
 a cover supported by the control handle to cover the suture spool, the cover being rotatable about the axis of rotation independent of the suture spool.

2. The endoscopic suturing device according to claim 1, wherein the control handle includes an actuator that is movable in a first direction that is parallel to the axis of rotation to control movement of the needle.

3. The endoscopic suturing device according to claim 2, wherein the suture spool is coaxial with the actuator.

4. The endoscopic suturing device according to claim 2, wherein the suture spool includes a bottom wall with a surface about which the suture is wound, the surface of the bottom wall being tapered at an angle relative to the axis of rotation.

5. The endoscopic suturing device according to claim 4, wherein the suture spool includes an end wall that is configured to urge the suture spool in an axial direction along the axis of rotation.

6. The endoscopic suturing device according to claim 5, wherein the surface of the bottom wall extends from the end wall and in an outward direction away from the axis of rotation.

7. The endoscopic suturing device according to claim 5, wherein the end wall is resilient.

8. The endoscopic suturing device according to claim 7, wherein at least a portion of the end wall is oriented at an angle that is non-perpendicular to the axis of rotation.

9. The endoscopic suturing device according to claim 1, wherein the cover is coaxial with the suture spool.

10. The endoscopic suturing device according to claim 1, wherein the control handle is constructed and arranged to provide external access to a portion of the suture.

11. The endoscopic suturing device according to claim 10, wherein the control handle has a suture access cavity that is open in an outward direction, the portion of the suture extending across the suture access cavity.

12. The endoscopic suturing device according to claim 11, wherein the cover is configured to expose the suture access cavity when rotated to a first position and overlie the suture access cavity when rotated to a second position.

13. The endoscopic suturing device according to claim 1, further comprising a suture tag that is releasably secured to the needle to carry the suture across the tissue suction chamber.

14. The endoscopic suturing device according to claim 13, further comprising a suture tag catch positioned at the distal end of the suturing capsule to retain the suture tag at the distal end of the suturing capsule when the suture tag is released from the needle and the needle is retracted to the proximal end of the suturing capsule.

15. The endoscopic suturing device according to claim 14, wherein the suture tag catch is configured to release the suture tag when the suture tag is locked to the needle and the needle is retracted to the proximal end of the suturing capsule.

16. The endoscopic suturing device according to claim 15, wherein the suture tag catch includes a plurality of resilient fingers that expand in an outward radial direction to receive and release the suture tag.

17. The endoscopic suturing device according to claim 16, wherein the resilient fingers are biased inwardly to a locked position to retain the suture tag when received in the suture tag catch.

18. An endoscopic tissue suturing device, comprising:
a suturing head that is endoscopically insertable into a patient, the suturing head constructed and arranged to capture tissue at a tissue capture region thereof;
a needle that is movable along a pathway that extends through the tissue capture region, the needle being adapted to penetrate tissue captured at the tissue capture region when the needle is extended in a distal direction from a proximal end to a distal end of the suturing head;
a control handle including an actuator that is coupled to the needle and movable in a first direction to control movement of the needle relative to the tissue capture region; and
a suture spool rotatably supported by the control handle about an axis of rotation that is parallel to the first direction, the suture spool including a length of suture that is coupled to the needle to form one or more stitches in tissue.

19. The endoscopic suturing device according to claim 18, wherein the suture spool is coaxial with the actuator.

20. The endoscopic suturing device according to claim 18, wherein the suture spool includes a bottom wall with a surface about which the suture is wound, the surface of the bottom wall being tapered at an angle relative to the axis of rotation.

21. The endoscopic suturing device according to claim 18, wherein the suture spool includes an end wall that is configured to urge the suture spool in an axial direction along the axis of rotation.

22. The endoscopic suturing device according to claim 21, wherein the end wall is resilient.

23. The endoscopic suturing device according to claim 22, wherein at least a portion of the end wall is oriented at an angle that is non-perpendicular to the axis of rotation.

24. The endoscopic suturing device according to claim 18, further comprising a cover supported by the control handle to cover the suture spool.

25. The endoscopic suturing device according to claim 24, wherein the cover is rotatable independent of the suture spool.

26. The endoscopic suturing device according to claim 25, wherein the cover is rotatable about the axis of rotation.

27. The endoscopic suturing device according to claim 18, further comprising a suture tag that is releasably secured to the needle to carry the suture across the tissue suction chamber, and a suture tag catch positioned at the distal end of the suturing head to retain the suture tag at the distal end of the suturing head when the suture tag is released from the needle and the needle is retracted to the proximal end of the suturing head.

28. The endoscopic suturing device according to claim 27, wherein the suture tag catch is configured to release the suture tag when the suture tag is locked to the needle and the needle is retracted to the proximal end of the suturing head.

29. The endoscopic suturing device according to claim 18, wherein the suturing head is mountable to a distal end of an endoscope, and the control handle is mountable to a proximal end of the endoscope.

30. An endoscopic tissue suturing device, comprising:
a suturing head that is endoscopically insertable into a patient, the suturing head constructed and arranged to capture tissue at a tissue region thereof;
a needle that is movable along a pathway that extends through the tissue capture region, the needle being adapted to penetrate tissue captured at the tissue capture region when the needle is moved along the pathway;
a control handle including an actuator that is coupled to the needle to control movement of the needle relative to the tissue capture region; and
a suture spool including a length of suture that is coupled to the needle to form one or more stitches in tissue, the suture spool being rotatably supported by the control handle about an axis of rotation, the suture spool including a bottom wall with a surface about which the suture is wound, the surface of the bottom wall being tapered at an angle relative to the axis of rotation.

31. The endoscopic suturing device according to claim 30, wherein the actuator is movable in a first direction that is parallel to the axis of rotation to control movement of the needle.

32. The endoscopic suturing device according to claim 30, wherein the suture spool includes an end wall that is configured to urge the suture spool in an axial direction along the axis of rotation.

33. The endoscopic suturing device according to claim 32, wherein the surface of the bottom wall extends from the end wall and in an outward direction away from the axis of rotation.

34. The endoscopic suturing device according to claim 32, wherein the end wall is resilient.

35. The endoscopic suturing device according to claim 34, wherein at least a portion of the end wall is oriented at an angle that is non-perpendicular to the axis of rotation.

36. The endoscopic suturing device according to claim 30, further comprising a cover supported by the control handle to cover the suture spool.

37. The endoscopic suturing device according to claim 36, wherein the cover is rotatable independent of the suture spool.

38. The endoscopic suturing device according to claim 37, wherein the coyer is rotatable about the axis of rotation.

39. The endoscopic suturing device according to claim 30, further comprising a suture tag that is releasably secured to the needle to carry the suture across the tissue suction chamber, and a suture tag catch positioned at the distal end of the suturing head to retain the suture tag at the distal end of the suturing head when the suture tag is released from the needle and the needle is retracted to the proximal end of the suturing head.

40. The endoscopic suturing device according to claim 39, wherein the suture tag catch is configured to release the suture tag when the suture tag is locked to the needle and the needle is retracted to the proximal end of the suturing head.

41. The endoscopic suturing device according to claim 30, wherein the suturing head is mountable to a distal end of an endoscope, and the control handle is mountable to a proximal end of the endoscope.

42. An endoscopic tissue suturing device, comprising:
a suturing head that is endoscopically insertable into a patient, the suturing head constructed and arranged to capture tissue;
a needle that is movable along a pathway that extends through a tissue capture region of the suturing head, the needle being adapted to penetrate tissue captured at the tissue capture region when the needle is moved along the pathway;
a control handle including an actuator that is coupled to the needle to control movement of the needle relative to the tissue capture region; and
a suture spool including a length of suture that is coupled to the needle to form one or more stitches in tissue, the suture spool being rotatable about an axis of rotation, the suture spool including a bottom wall with a surface about which the suture is wound and an end wall located at an end of the bottom wall to retain the suture on the suture spool, the end wall being constructed and arranged to urge the suture spool in an axial direction along the axis of rotation.

43. The endoscopic suturing device according to claim 42, wherein the end wall is resilient.

44. The endoscopic suturing device according to claim 42, wherein at least a portion of the end wall is oriented at an angle that is non-perpendicular to the axis of rotation.

45. The endoscopic suturing device according to claim 42, wherein the surface of the bottom wall is tapered at an angle relative to the axis of rotation.

46. The endoscopic suturing device according to claim 45, wherein the surface of the bottom wall extends from the end wall and in an outward direction away from the axis of rotation.

47. The endoscopic suturing device according to claim 42, wherein the actuator is movable in a first direction that is parallel to the axis of rotation to control movement of the needle.

48. The endoscopic suturing device according to claim 47, wherein the suture spool is coaxial with the actuator.

49. The endoscopic suturing device according to claim 42, further comprising a cover supported by the control handle to cover the suture spool.

50. The endoscopic suturing device according to claim 49, wherein the cover is rotatable independent of the suture spool.

51. The endoscopic suturing device according to claim 50, wherein the cover is rotatable about the axis of rotation.

52. The endoscopic suturing device according to claim 42, further comprising a suture tag that is releasably secured to the needle to carry the suture across the tissue suction chamber, and a suture tag catch positioned at the distal end of the suturing head to retain the suture tag at the distal end of the suturing head when the suture tag is released from the needle and the needle is retracted to the proximal end of the suturing head.

53. The endoscopic suturing device according to claim 52, wherein the suture tag catch is configured to release the suture tag when the suture tag is locked to the needle and the needle is retracted to the proximal end of the suturing head.

54. The endoscopic suturing device according to claim 42, wherein the suturing head is mountable to a distal end of an endoscope, and the control handle is mountable to a proximal end of the endoscope.

55. An endoscopic tissue suturing device, comprising:
a suturing head that is endoscopically insertable into a patient, the suturing head constructed and arranged to capture tissue;
a needle that is movable along a pathway that extends through a tissue capture region of the suturing head, the needle being adapted to penetrate tissue captured at the tissue capture region when the needle is moved along the pathway;
a control handle including an actuator that is coupled to the needle to control movement of the needle relative to the tissue capture region; and
a suture spool including a length of suture that is coupled to the needle to form one or more stitches in tissue, the suture spool being rotatably housed within the control handle about an axis of rotation, the control handle including a plurality of passages to guide the suture from the suture spool toward a distal end of the control handle, the control handle further including a suture access cavity located between the suture spool and the distal end, the suture access cavity being open in an outward direction to provide external access to a portion of the suture, the portion of the suture extending across the suture access cavity from a first end to a second end thereof, the plurality of passages including a suture passage to guide suture from the suture spool to the first end of the suture access cavity and one or more interior passages to guide suture from the second end of the suture access cavity toward the distal end of the control handle.

56. The endoscopic suturing device according to claim 55, further comprising a cover supported by the control handle to cover the suture spool.

57. The endoscopic suturing device according to claim 56, wherein the cover is configured to expose the suture access cavity when oriented in a first position and overlie the suture access cavity when oriented in a second position.

58. The endoscopic suturing device according to claim 56, wherein the cover is rotatable independent of the suture spool.

59. The endoscopic suturing device according to claim 58, wherein the cover is rotatable about the axis of rotation.

60. The endoscopic suturing device according to claim 55, wherein the suture spool includes a bottom wall with a surface about which the suture is wound, the surface of the bottom wall being tapered at an angle relative to the axis of rotation.

61. The endoscopic suturing device according to claim 60, wherein the suture spool includes an end wall that is configured to urge the suture spool in an axial direction along the axis of rotation.

62. The endoscopic suturing device according to claim 61, wherein the surface of the bottom wall extends from the end wall and in an outward direction away from the axis of rotation.

63. The endoscopic suturing device according to claim 62, wherein the end wall is resilient.

64. The endoscopic suturing device according to claim 63, wherein at least a portion of the end wall is oriented at an angle that is non-perpendicular to the axis of rotation.

65. The endoscopic suturing device according to claim 55, wherein the actuator is movable in a first direction that is parallel to the axis of rotation to control movement of the needle.

66. The endoscopic suturing device according to claim 65, wherein the suture spool is coaxial with the actuator.

67. The endoscopic suturing device according to claim 55, further comprising a suture tag that is releasably secured to the needle to carry the suture across the tissue suction chamber, and a suture tag catch positioned at the distal end of the suturing head to retain the suture tag at the distal end of the suturing head when the suture tag is released from the needle and the needle is retracted to the proximal end of the suturing head.

68. The endoscopic suturing device according to claim 67, wherein the suture tag catch is configured to release the suture tag when the suture tag is locked to the needle and the needle is retracted to the proximal end of the suturing head.

69. The endoscopic suturing device according to claim 55, wherein the suturing head is mountable to a distal end of an endoscope, and the control handle is mountable to a proximal end of the endoscope.

* * * * *